(12) United States Patent
Miller et al.

(10) Patent No.: US 10,542,981 B2
(45) Date of Patent: Jan. 28, 2020

(54) ATRAUMATIC STAPLING HEAD FEATURES FOR CIRCULAR SURGICAL STAPLER

(71) Applicant: Ethicon Endo-Surgery, LLC, Guaynabo, PR (US)

(72) Inventors: Christopher C. Miller, Loveland, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 416 days.

(21) Appl. No.: 15/350,593

(22) Filed: Nov. 14, 2016

(65) Prior Publication Data

US 2018/0132848 A1    May 17, 2018

(51) Int. Cl.
  *A61B 17/072* (2006.01)
  *A61B 17/115* (2006.01)
  *A61B 17/00* (2006.01)
  *A61B 90/00* (2016.01)

(52) U.S. Cl.
  CPC .... *A61B 17/07207* (2013.01); *A61B 17/1155* (2013.01); *A61B 2017/00398* (2013.01); *A61B 2017/00734* (2013.01); *A61B 2017/07214* (2013.01); *A61B 2017/07221* (2013.01); *A61B 2017/07257* (2013.01); *A61B 2017/07271* (2013.01); *A61B 2017/07278* (2013.01); *A61B 2090/0811* (2016.02)

(58) Field of Classification Search
  CPC .......... A61B 2017/07278; A61B 2017/07221; A61B 2017/07271; A61B 2017/07257; A61B 2017/07214; A61B 2017/00734; A61B 2017/00398; A61B 17/1155; A61B 17/07207; A61B 2090/0811
  See application file for complete search history.

(56) References Cited

U.S. PATENT DOCUMENTS

| 5,205,459 A | 4/1993 | Brinkerhoff et al. |
| 5,271,544 A | 12/1993 | Fox et al. |
| 5,275,322 A | 1/1994 | Wolf et al. |

(Continued)

FOREIGN PATENT DOCUMENTS

| CN | 2 500 264 Y | 7/2002 |
| CN | 103 431 886 A | 12/2013 |

(Continued)

OTHER PUBLICATIONS

U.S. Appl. No. 14/864,310, filed Sep. 24, 2015.

(Continued)

*Primary Examiner* — Chelsea E Stinson
*Assistant Examiner* — Thomas M Wittenschlaeger
(74) *Attorney, Agent, or Firm* — Frost Brown Todd LLC

(57) ABSTRACT

An apparatus includes a body, a shaft assembly, a stapling head assembly, and an anvil. The stapling head assembly includes an annular deck member, a plurality of staples, and a driver. The deck member includes a deck surface that has a curved profile defined by a curve extending from the inner diameter of the deck member to the outer diameter of the deck member. The deck member further includes an outer array of staple openings and an inner array of staple openings. The driver is operable to drive the staples through the staple openings. The anvil is operable to compress tissue against the first deck surface.

20 Claims, 26 Drawing Sheets

(56) References Cited

U.S. PATENT DOCUMENTS

| | | | |
|---|---|---|---|
| 5,285,945 | A | 2/1994 | Brinkerhoff et al. |
| 5,292,053 | A | 3/1994 | Smith et al. |
| 5,333,773 | A | 8/1994 | Main et al. |
| 5,350,104 | A | 9/1994 | Main et al. |
| 5,533,661 | A | 7/1996 | Main et al. |
| 7,794,475 | B2 | 9/2010 | Hess et al. |
| 8,910,847 | B2 | 12/2014 | Nalagatla et al. |
| 9,289,207 | B2 | 3/2016 | Shelton, IV |
| 9,463,022 | B2 | 10/2016 | Swayze et al. |
| 9,498,222 | B2 | 11/2016 | Scheib et al. |
| 9,532,783 | B2 | 1/2017 | Swayze et al. |
| 9,572,573 | B2 | 2/2017 | Scheib et al. |
| 2003/0178465 | A1* | 9/2003 | Bilotti ............... A61B 17/115 227/180.1 |
| 2012/0168487 | A1* | 7/2012 | Holsten ........... A61B 17/00491 227/176.1 |
| 2013/0026209 | A1* | 1/2013 | Mozdzierz ......... A61B 17/1155 227/180.1 |
| 2014/0103092 | A1* | 4/2014 | Kostrzewski .... A61B 17/07207 227/178.1 |
| 2014/0151430 | A1 | 6/2014 | Scheib et al. |
| 2014/0158747 | A1 | 6/2014 | Measamer et al. |
| 2014/0166728 | A1 | 6/2014 | Swayze et al. |
| 2015/0014393 | A1* | 1/2015 | Milliman ............... A61B 90/98 227/180.1 |
| 2015/0083772 | A1 | 3/2015 | Miller et al. |
| 2015/0083773 | A1 | 3/2015 | Measamer et al. |
| 2015/0083774 | A1 | 3/2015 | Measamer et al. |
| 2015/0083775 | A1 | 3/2015 | Leimbach et al. |
| 2015/0297235 | A1* | 10/2015 | Harris ................ G06F 11/1425 227/176.1 |
| 2015/0297236 | A1* | 10/2015 | Harris ................ A61B 17/0644 227/176.1 |
| 2015/0327862 | A1* | 11/2015 | Kostrzewski .... A61B 17/07207 227/178.1 |
| 2016/0100837 | A1 | 4/2016 | Huang et al. |
| 2016/0374666 | A1 | 12/2016 | DiNardo et al. |
| 2016/0374672 | A1 | 12/2016 | Bear et al. |
| 2017/0281188 | A1* | 10/2017 | Shelton, IV ....... A61B 17/0644 |
| 2017/0319207 | A1* | 11/2017 | Shelton, IV ..... A61B 17/07207 |
| 2018/0168627 | A1* | 6/2018 | Weaner ........... A61B 17/07207 |

FOREIGN PATENT DOCUMENTS

| | | |
|---|---|---|
| CN | 104 490 441 A | 4/2015 |
| EP | 1 316 290 A2 | 6/2003 |
| JP | S60-139240 A | 7/1985 |

OTHER PUBLICATIONS

U.S. Appl. No. 15/350,513, filed Nov. 14, 2016.
U.S. Appl. No. 15/350,621, filed Nov. 14, 2016.
U.S. Appl. No. 15/350,624, filed Nov. 14, 2016.
U.S. Appl. No. 16/117,600, and.
U.S. Appl. No. 16/117,621.
European Search Report and Written Opinion dated Mar. 14, 2018 for Application No. EP 17201387.2, 12 pgs.
International Search Report and Written Opinion dated Aug. 8, 2017 for Application No. PCT/US2017/035113, 15 pgs.

\* cited by examiner

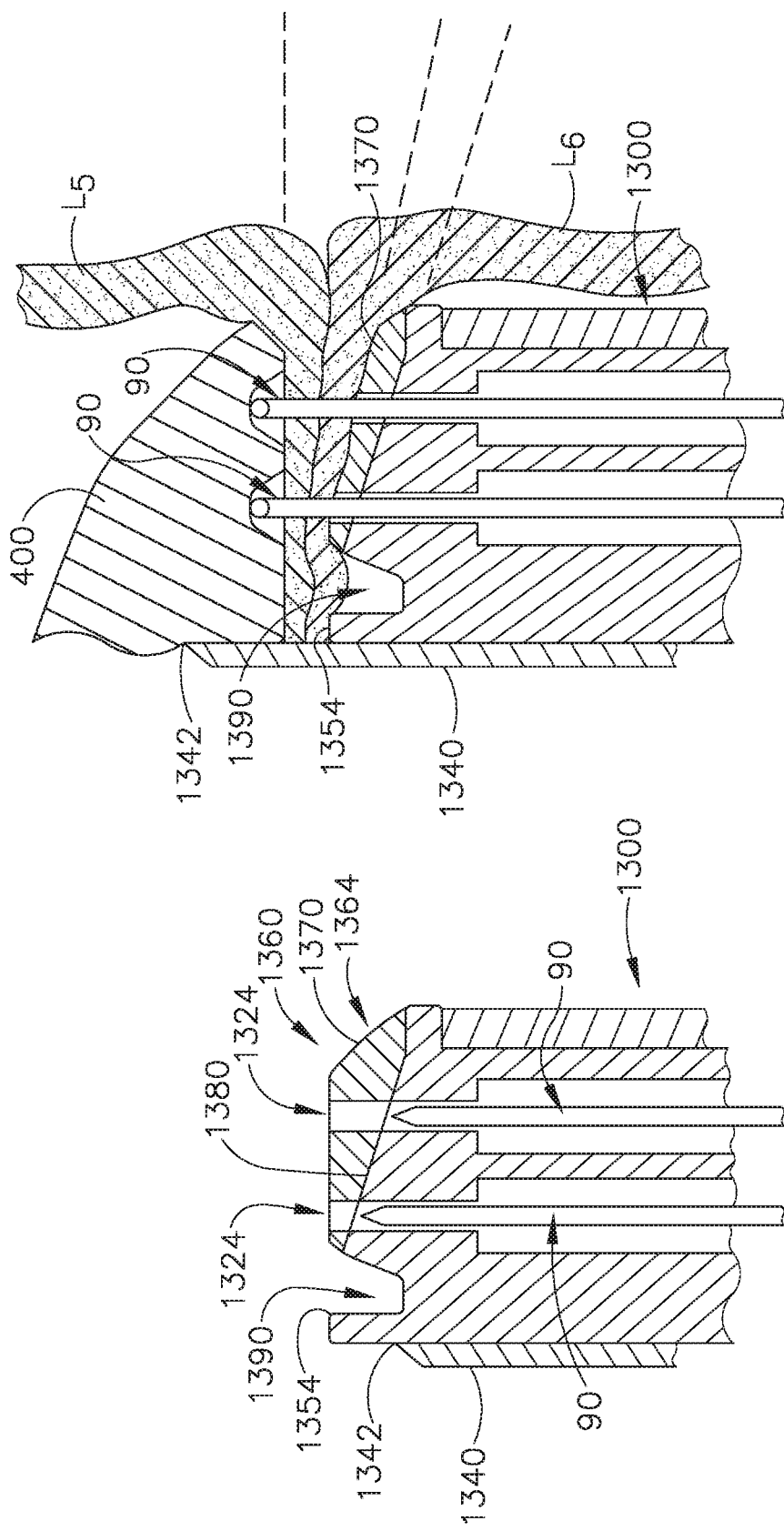

ATRAUMATIC STAPLING HEAD FEATURES FOR CIRCULAR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 25 depicts a partial cross-sectional view of the stapling head assembly of FIG. 24;

FIG. 26 depicts a partial cross-sectional view of an exemplary anvil compressing tissue against the stapling head assembly of FIG. 24;

Figure 1:
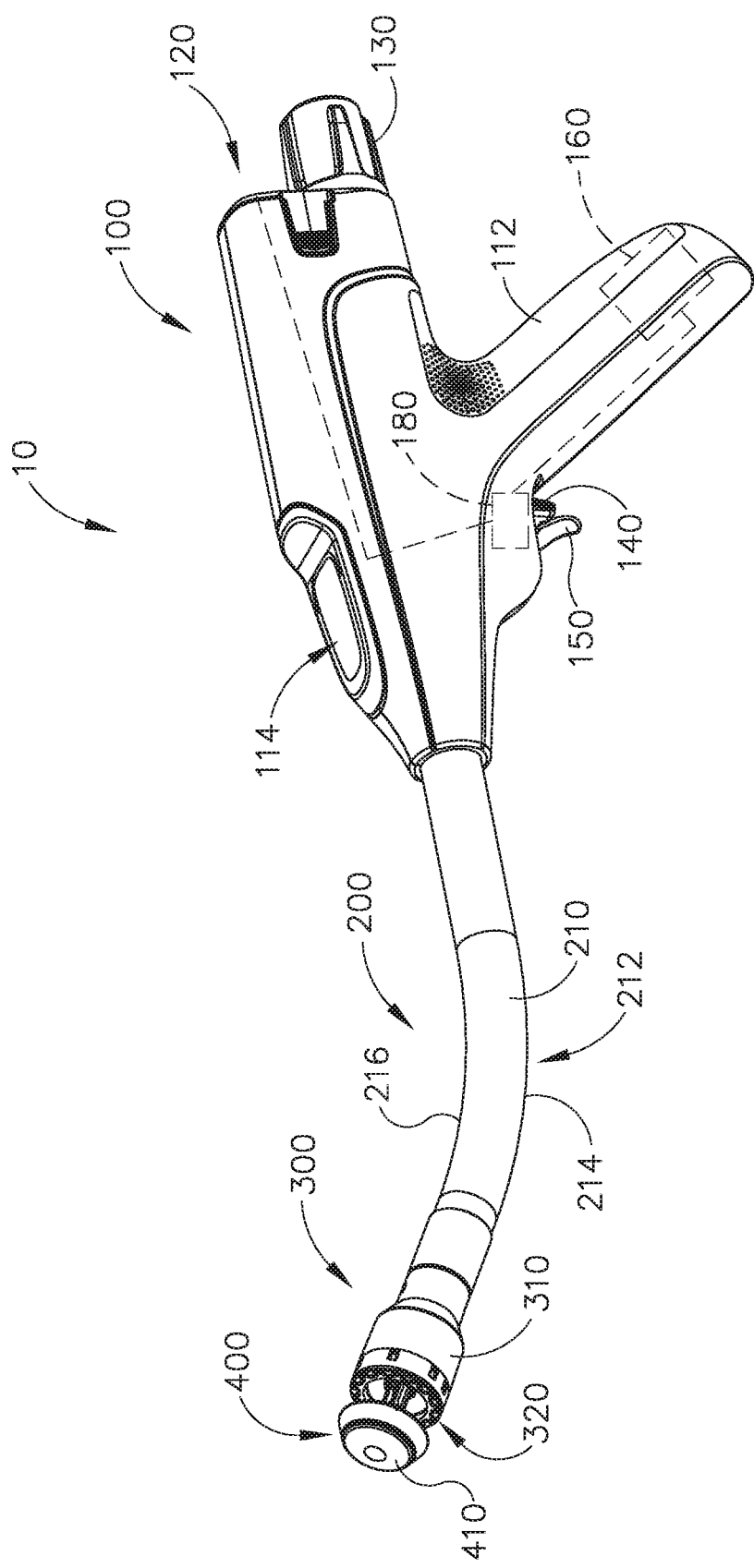
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
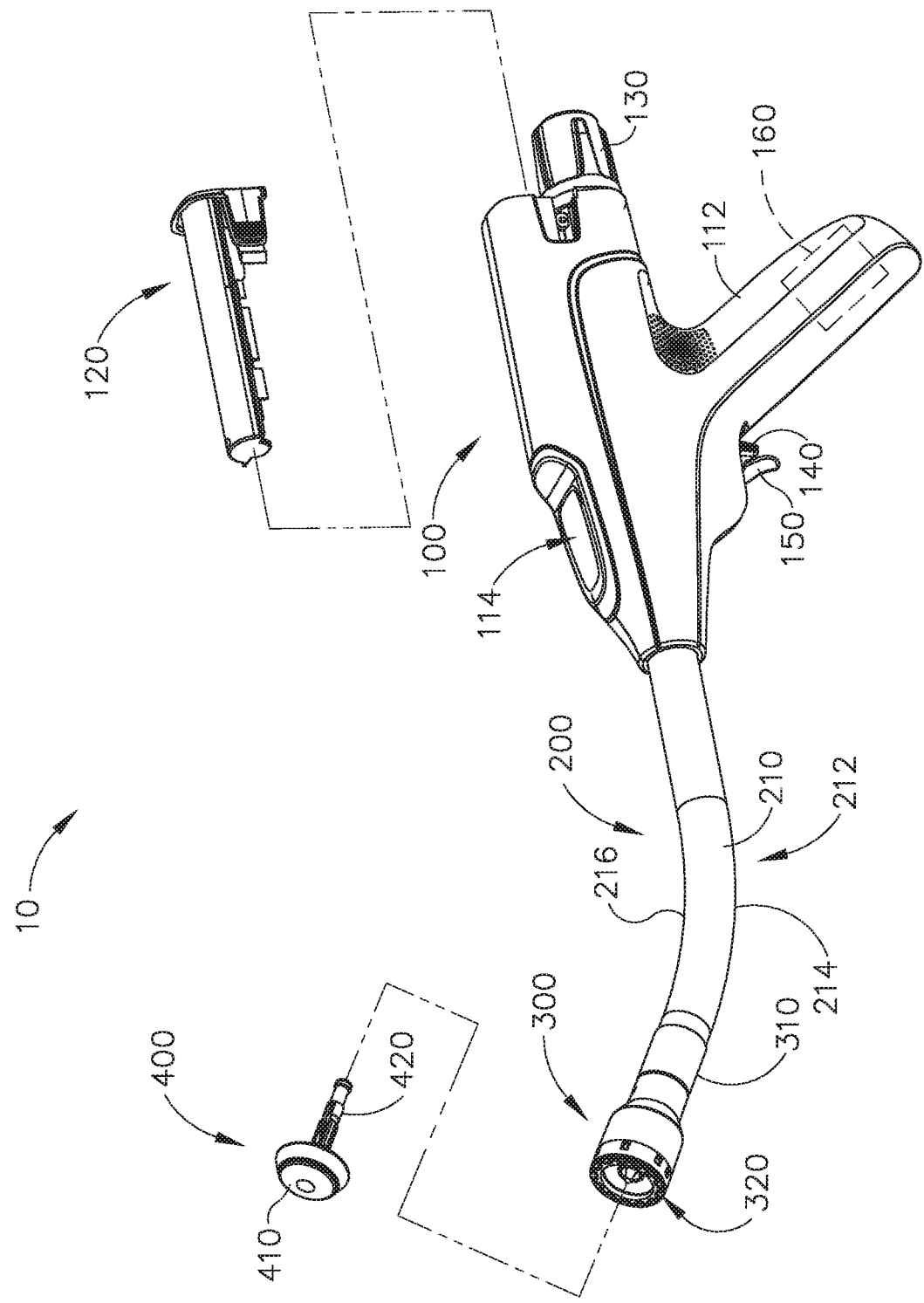
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), an anvil (400), and a removable battery pack (120). Each of these components will be described in greater detail below. It should be understood that, in addition to or in lieu of the following, instrument (10) may be further constructed and operable in accordance with at least some of the teachings of U.S. patent application Ser. No. 14/751,612, entitled "Method of Applying an Annular Array of Staples to Tissue," filed Jun. 26, 2015, issued as U.S. Pat. No. 10,478,189 on Nov. 19, 2019; U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

A. Exemplary Tissue Engagement Features of Circular Stapling Instrument

Figure 3:
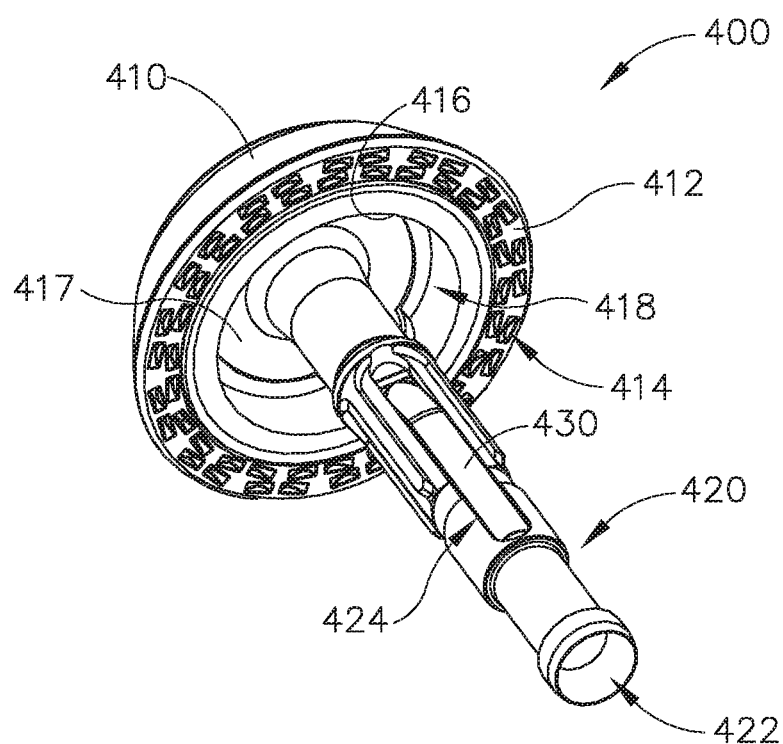
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Figure 4:
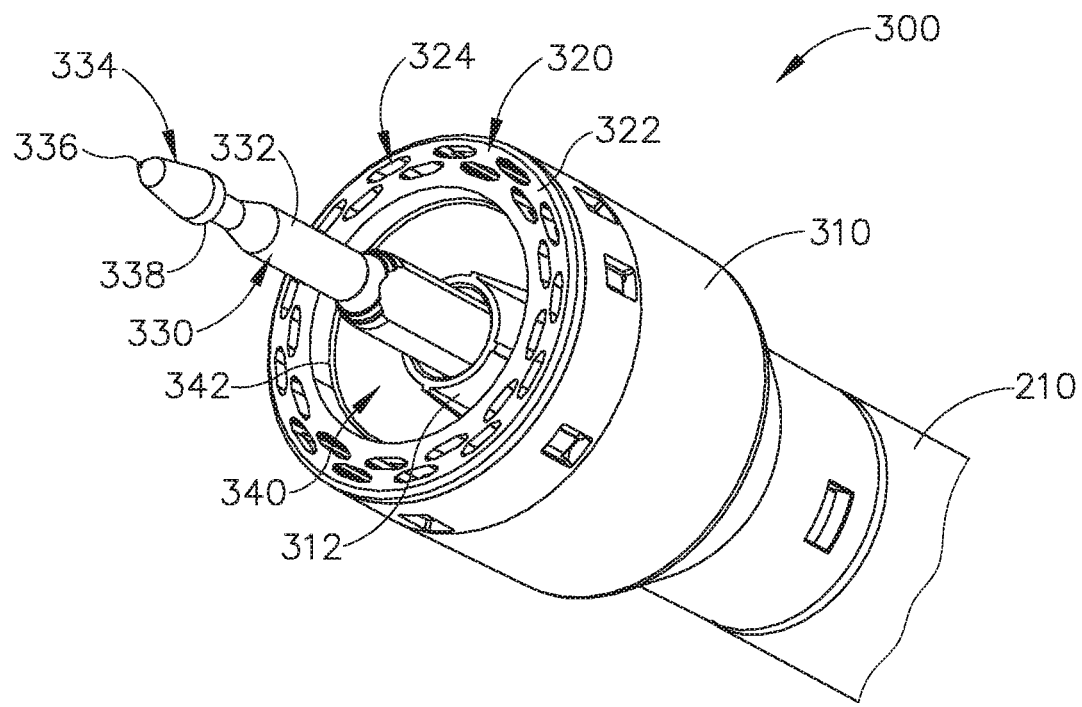
FIG. 4 depicts a perspective view of the stapling head assembly of the circular stapler of FIG. 1.
Figure 5:
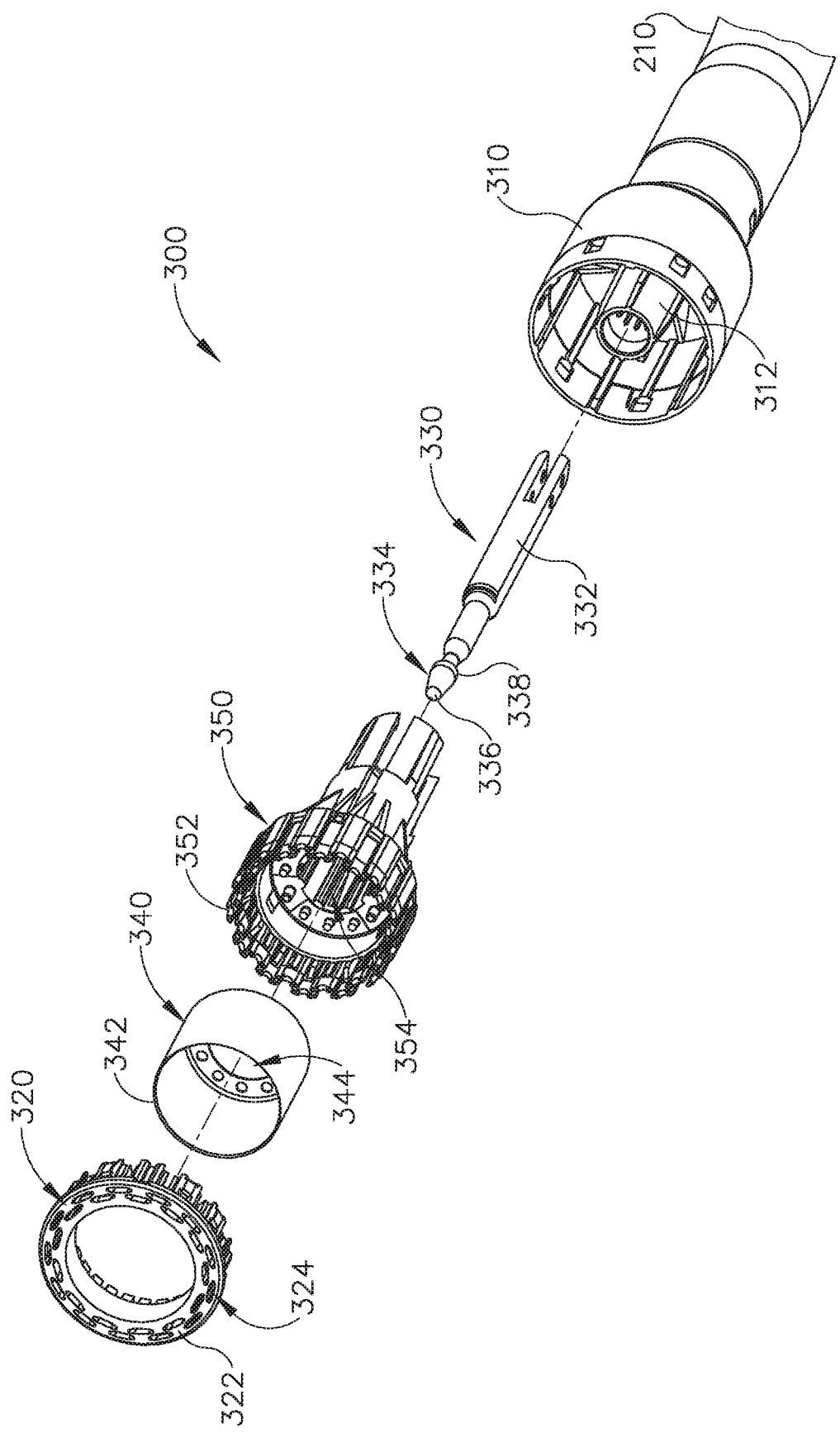
FIG. 5 depicts an exploded perspective view of the stapling head assembly of FIG. 4.

Stapling head assembly (300) is located at the distal end of shaft assembly (200). As shown in FIGS. 1-2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4-5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (420). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Deck member (320) defines an inner diameter that is just slightly larger than the outer diameter defined by knife member (340). Deck member (320) is thus configured to allow knife member (340) to translate distally to a point where cutting edge (342) is distal to deck surface (322).

Figure 6:
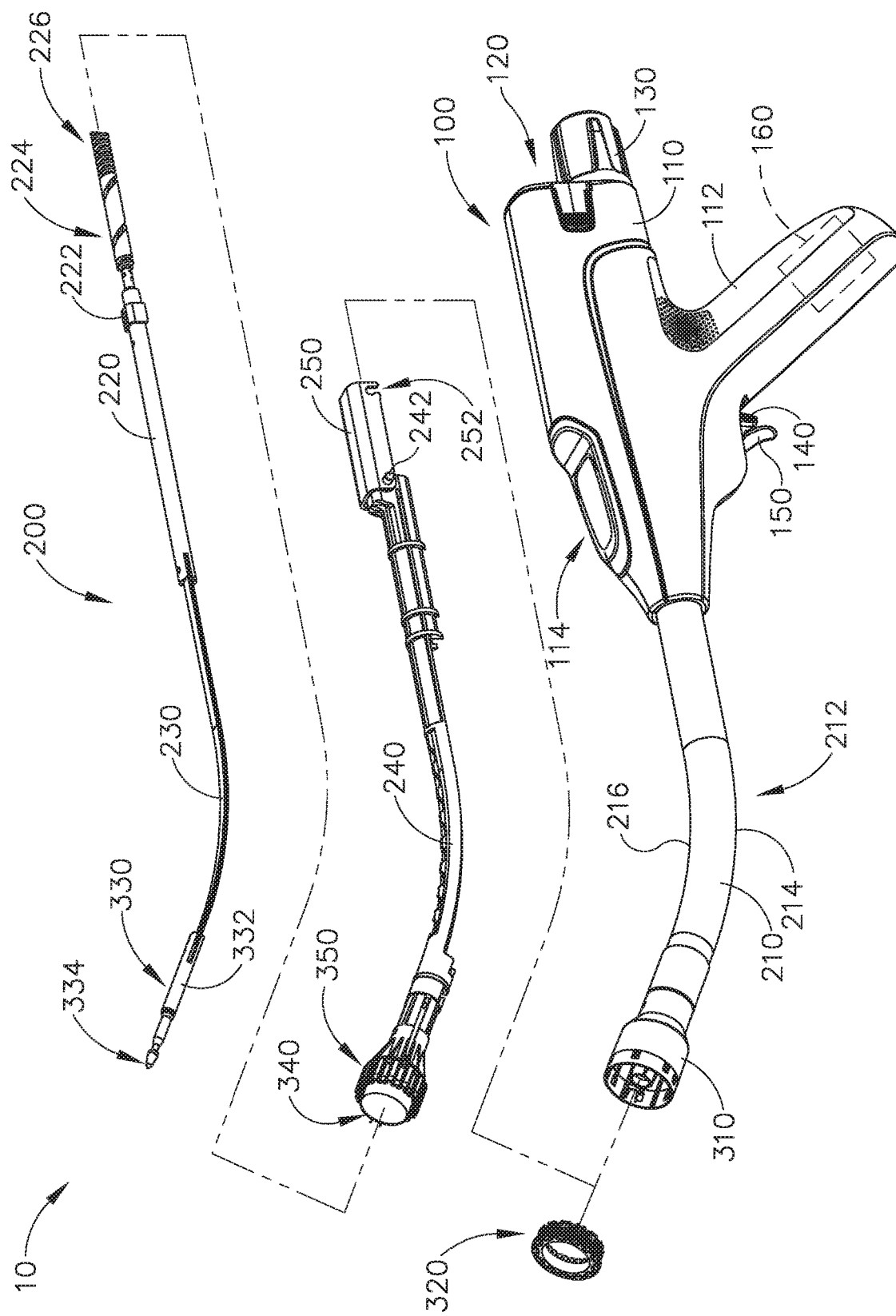
FIG. 6 depicts an exploded perspective view of the circular stapler of FIG. 1, with portions of the shaft assembly shown separately from each other.

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section (212) that is configured to facilitate positioning of stapling head assembly (300) within a patient's colon as described below. Curved section (212) includes an inner curve (216) and an outer curve (214).

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

B. Exemplary User Input Features of Circular Stapling Instrument

As shown in FIG. 1, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil relative to stapling head assembly (300). It should also be understood that knob (130)

may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance between opposing surfaces (412, 322) of anvil (400) and stapling head assembly (300) until a suitable gap distance has been achieved.

In the present example, handle assembly (100) comprises a user feedback feature (114) that is configured to provide the operator with visual feedback indicating the positioning of anvil (400) in relation to stapling assembly (300). The operator may thus observe user feedback feature (114) while rotating knob (130), to confirm whether the suitable gap distance between anvil (400) and stapling assembly (300) has been achieved. By way of example only, user feedback feature (114) may be configured and operable in accordance with at least some of the teachings of U.S. patent application Ser. No. 14/751,612, entitled "Method of Applying an Annular Array of Staples to Tissue," filed Jun. 26, 2015, issued as U.S. Pat. No. 10,478,189 on Nov. 19, 2019, the disclosure of which is incorporated by reference herein. Other suitable forms of providing user feedback will be apparent to those of ordinary skill in the art in view of the teachings herein.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range.

In the present example, firing trigger (150) of the present example includes an integral actuation paddle, such as the paddle shown and described in U.S. patent application Ser. No. 14/751,231, entitled "Surgical Stapler with Reversible Motor," filed Jun. 26, 2015, issued as U.S. Pat. No. 10,456,134 on Oct. 29, 2019, the disclosure of which is incorporated by reference herein. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) as described in greater detail below.

Battery pack (120) is operable to provide electrical power to a motor (160) as noted above. Battery pack (120) may be removably coupled with handle assembly (100) through a snap fit or in any other suitable fashion. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery back (120) cannot be removed from handle assembly (100).

C. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
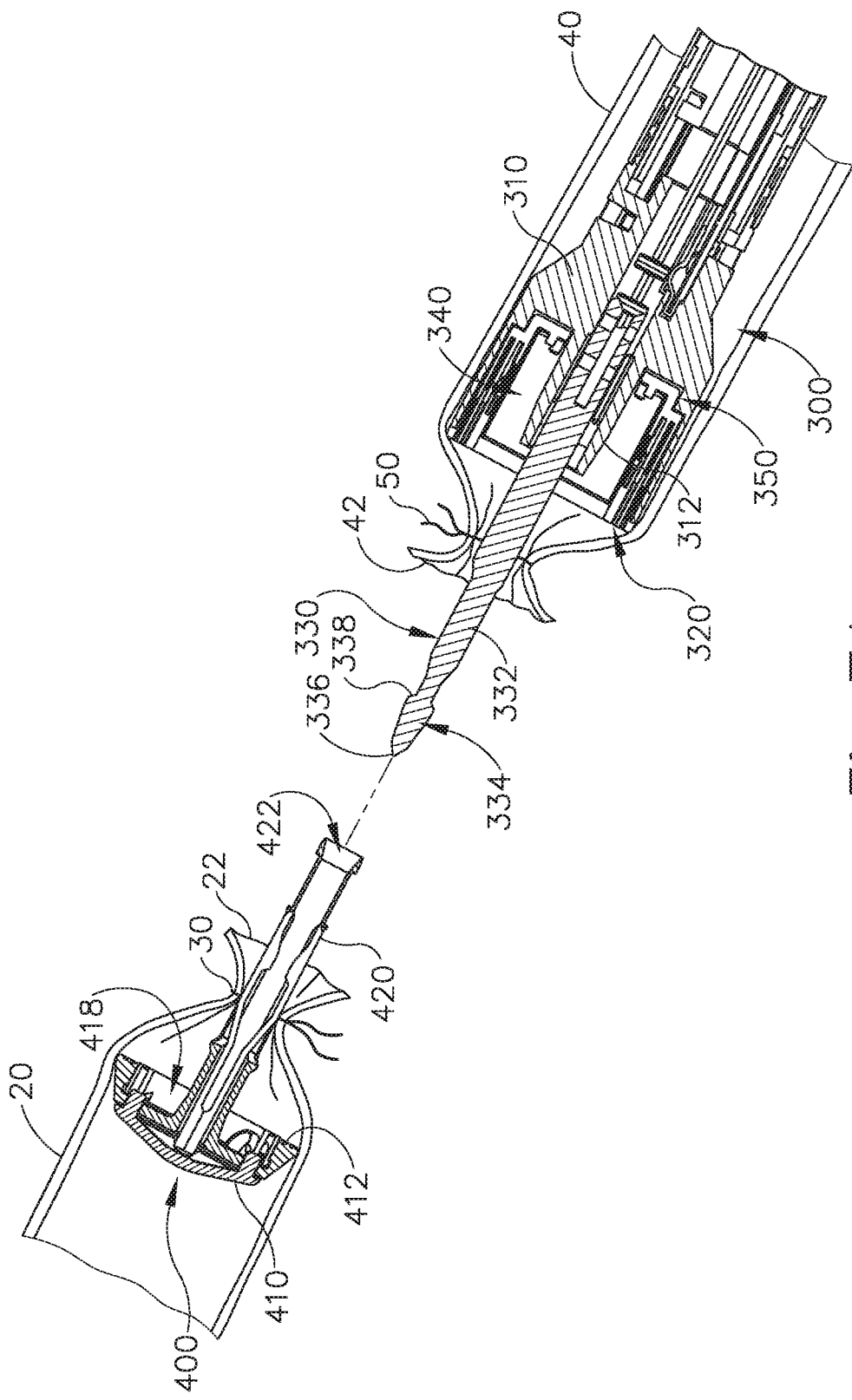
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. By way of example only, the surgical procedure may be performed laparoscopically in accordance with at least some of the teachings of U.S. Pub. No. 2016/0100837, entitled "Surgical Stapling Apparatus Comprising A Tissue Stop," published Apr. 14, 2016, issued as U.S. Pat. No. 10,076,325 on Sep. 18, 2018, the disclosure of which is incorporated by reference herein; and/or U.S. patent application Ser. No. 14/864,310, entitled "Apparatus and Method for Forming a Staple Line with Trocar Passageway," filed Sep. 24, 2015, issued as U.S. Pat. No. 10,485,548 on Nov. 26, 2019, the disclosure of which is incorporated by reference herein. Various other suitable ways in which instrument (10) may be used to form an anastomosis (70) in a laparoscopic procedure will be apparent to those of ordinary skill in the art in view of the teachings herein.

As shown in FIG. 7A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Figure 7B:
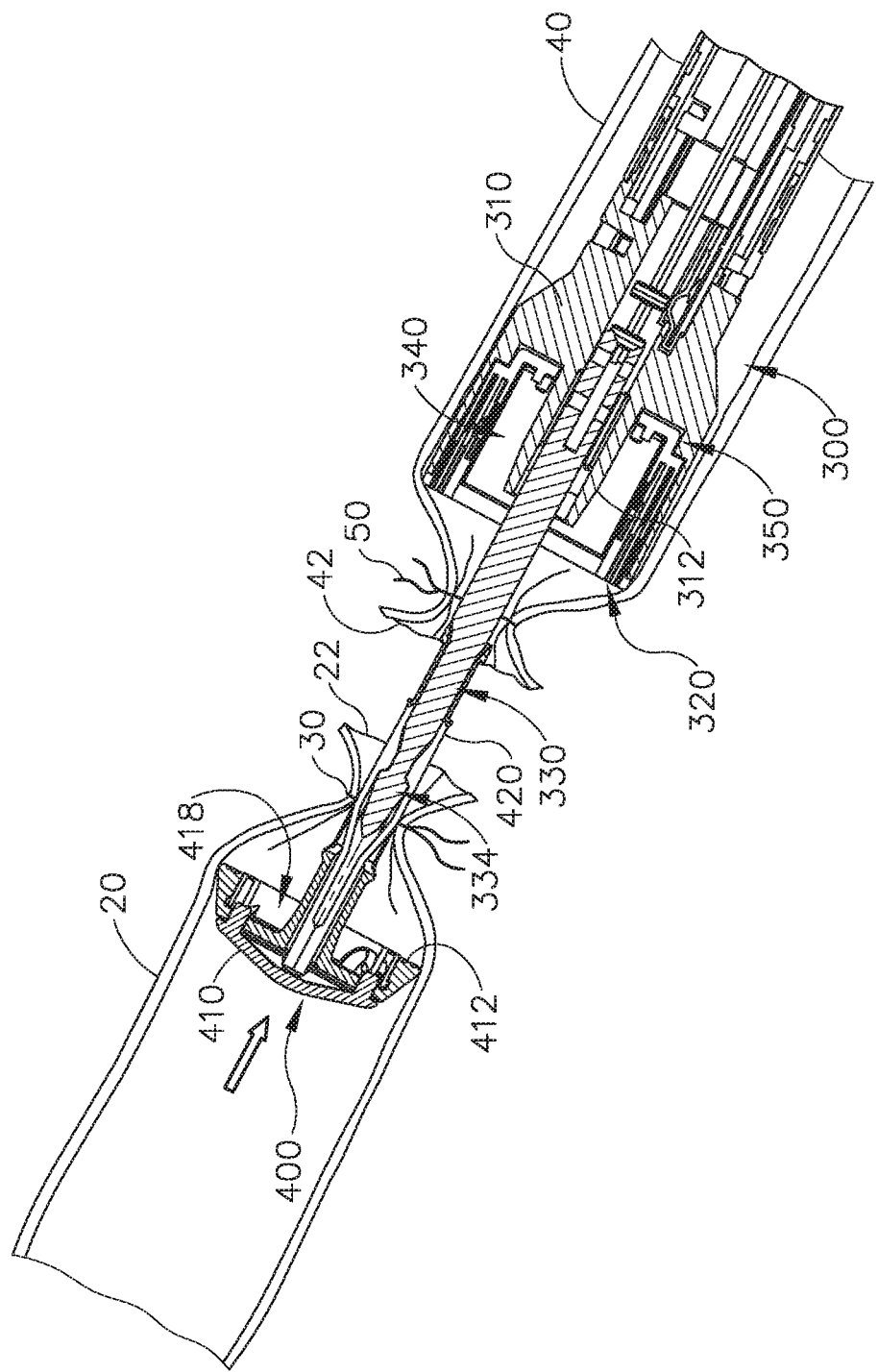
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
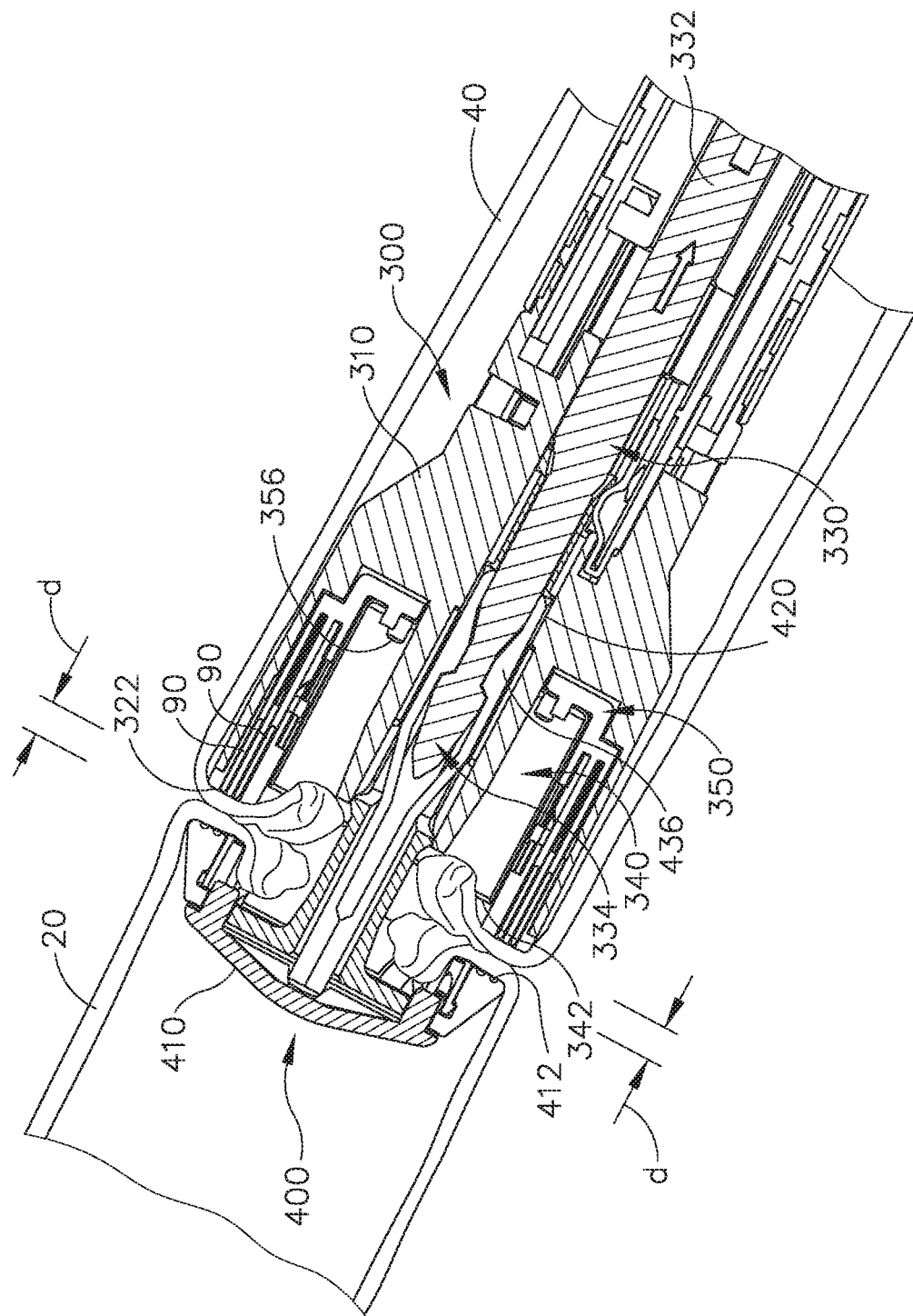
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding handle assembly (100) stationary via pistol grip (112). This rotation of knob (130) causes trocar (330) and anvil (400) to retract proximally, as described above. As shown in FIG. 7C, this proximal retraction of trocar (330) and anvil (400) compresses the tissue of tubular anatomical structures (20, 40) between surfaces (412, 322) of anvil (400) and stapling head assembly (300). The operator observes user feedback feature (114) to determine whether the gap distance (d) between opposing surfaces (412, 322) of anvil (400) and stapling head assembly (300) is appropriate; and makes any necessary adjustments via knob (130).

Figure 7D:
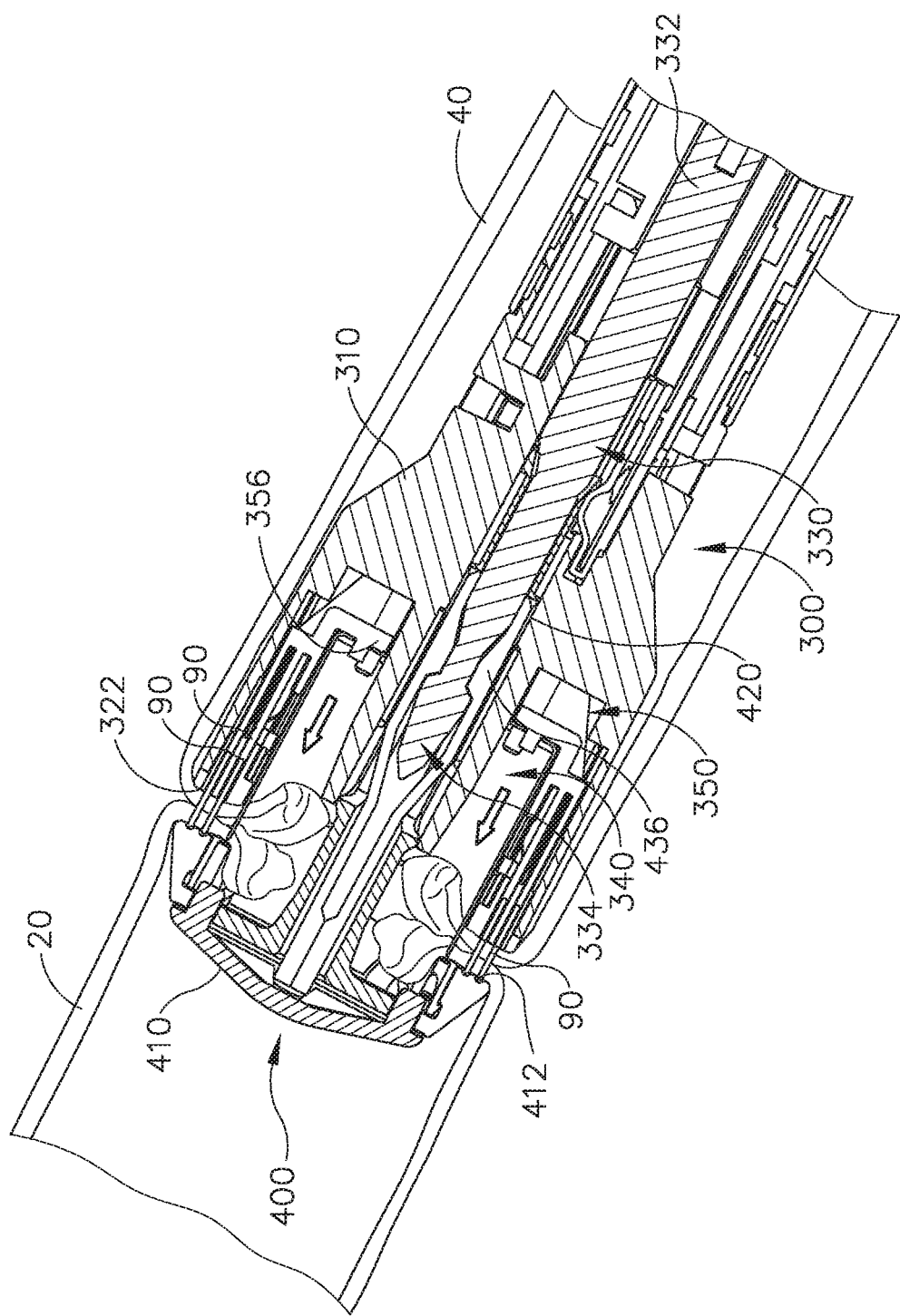
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator actuates safety trigger (140) to enable actuation of firing trigger (150). The operator then actuates firing trigger (150). This actuation of firing trigger (150) in turn actuates a switch of motor activation module (180), which in turn activates motor (160) to thereby actuate stapling head assembly (300) by driving knife member (340) and staple driver member (350) distally as shown in FIG. 7D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when knife member (340) completes a full distal range of motion from the position shown in FIG. 7C to the position shown in FIG. 7D. The drive mechanism for knife member (340) may provide an increasing mechanical advantage as knife member (340) reaches the end of its distal movement, thereby providing greater force by which to break washer (417). Of course, breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and cutting edge (342).

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together, thereby coupling tubular anatomical structure (20) with tubular anatomical structure (40).

Figure 7E:
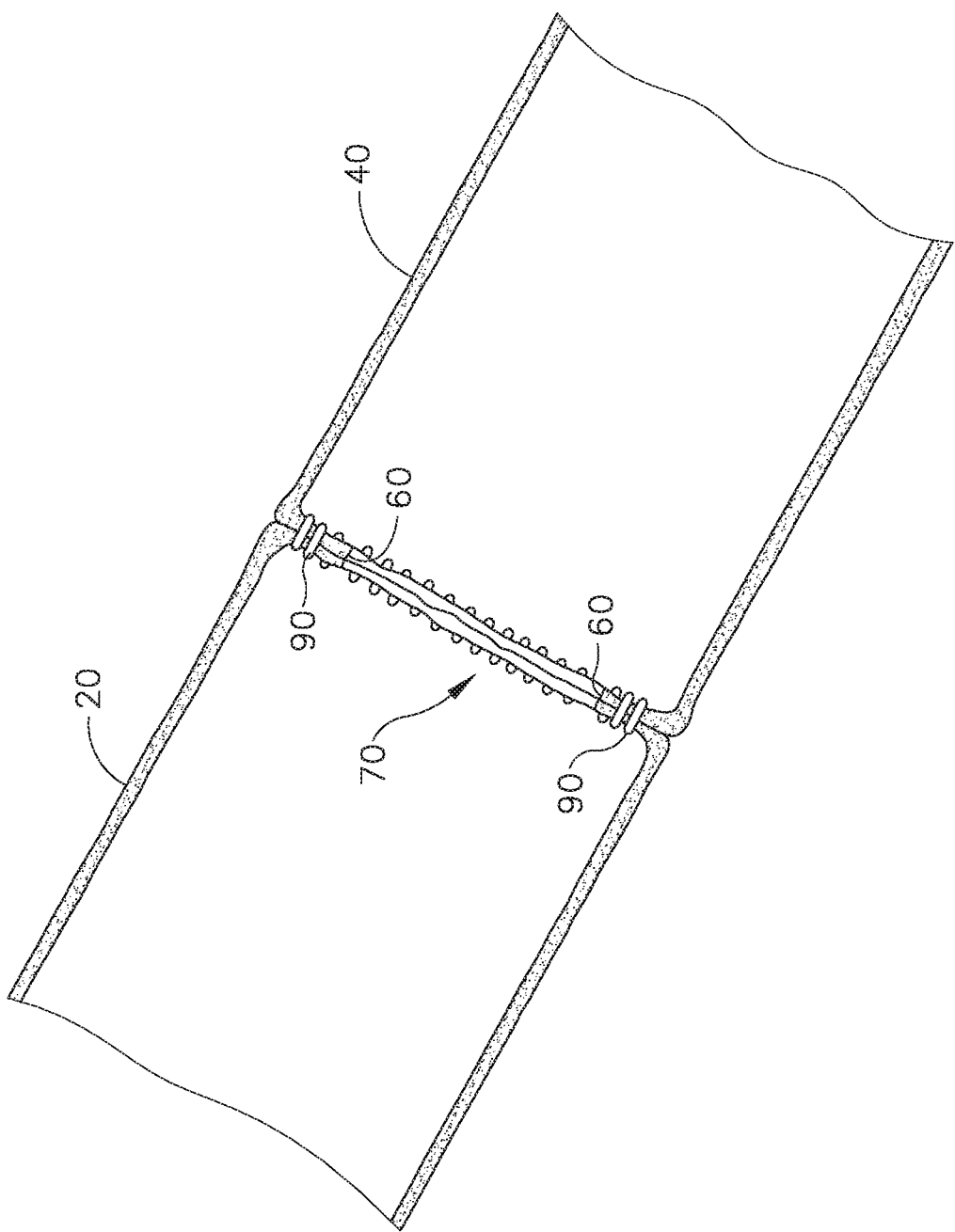
FIG. 7E depicts a cross-sectional side view of the first and second sections of the digestive tract of FIG. 7A joined together at an end-to-end anastomosis.

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Exemplary Alternative Stapling Head Assembly

Figure 8:
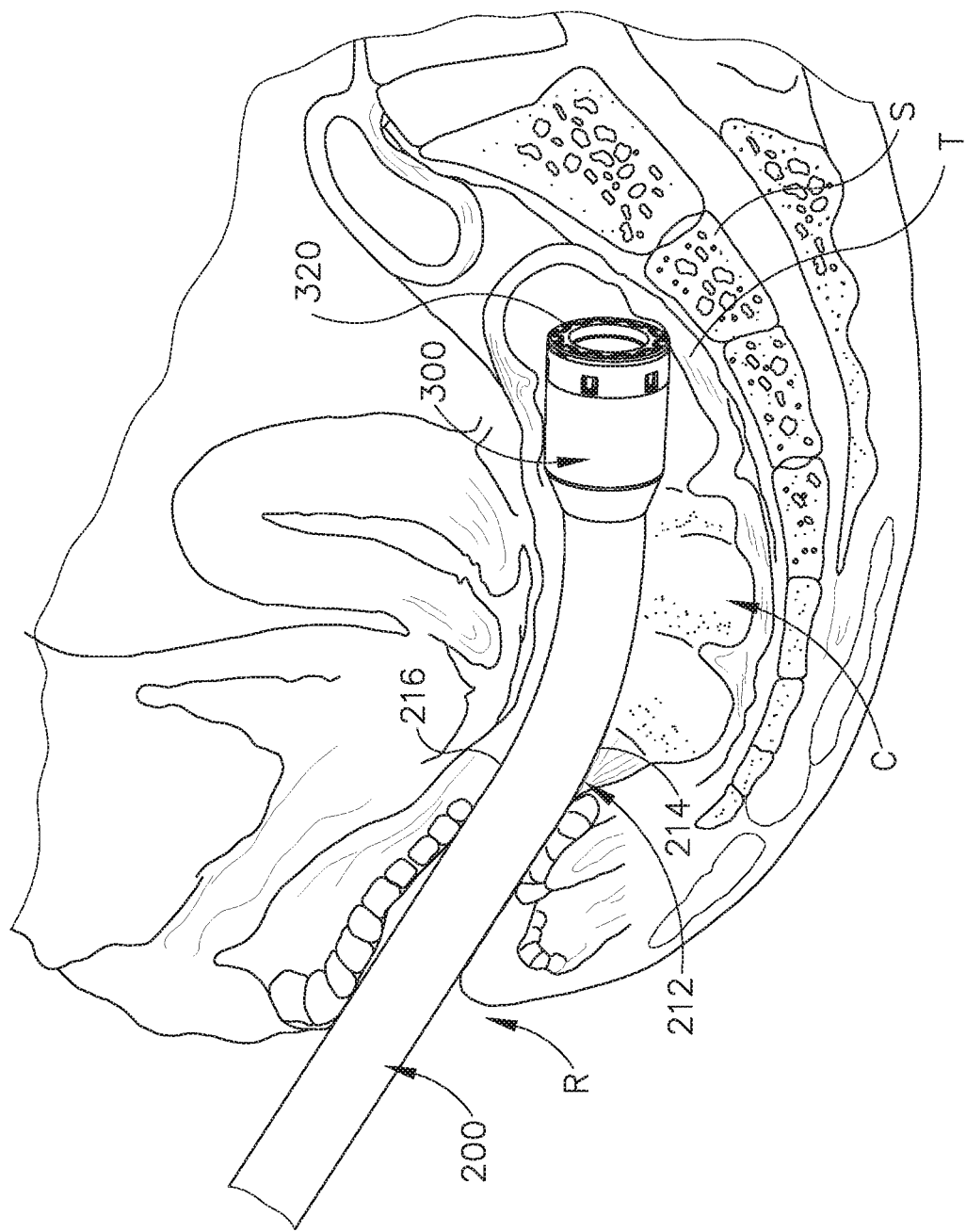
FIG. 8 depicts a partial perspective view of the stapling head assembly and shaft assembly of the circular stapler of FIG. 1 inserted in a patient's colon, with the stapling head assembly positioned near the patient's sacrum, and with the patient's anatomy shown in cross-section.

As noted above, in some instances, anatomical structures (20, 40) may comprise sections of a patient's colon. FIG. 8 shows stapling head assembly (300) and a distal portion of shaft assembly (200) disposed in a patient's colon (C). As shown, stapling head assembly (300) and shaft assembly (200) are inserted via the patient's rectum (R). As also shown, the curvature of curved section (212) is configured to generally complement the curvature of the patient's colon (C). Nevertheless, as also shown in FIG. 8, there may be instances where deck member (320) tends to compress tissue (T) of the patient's colon (C) against the patient's sacrum (S) and/or some other substantially rigid anatomical structure. Depending on the angle at which the operator has inserted stapling head assembly (300) and shaft assembly (200), and/or depending on the force that the operator is applying to stapling head assembly (300) and shaft assembly (200) during insertion, the tissue (T) of the patient's colon (C) may become damaged (e.g., torn) when the tissue (T) is pinched between stapling head assembly (300) and the patient's sacrum (S). In versions where deck member (320) has tissue gripping features and/or other protruding features (e.g., staple guidance features, etc.), such features may increase the risk of damage to the tissue (T) of the patient's colon (C) as stapling head assembly (300) and shaft assembly (200) are being inserted into the patient's colon (C).

Figure 9:
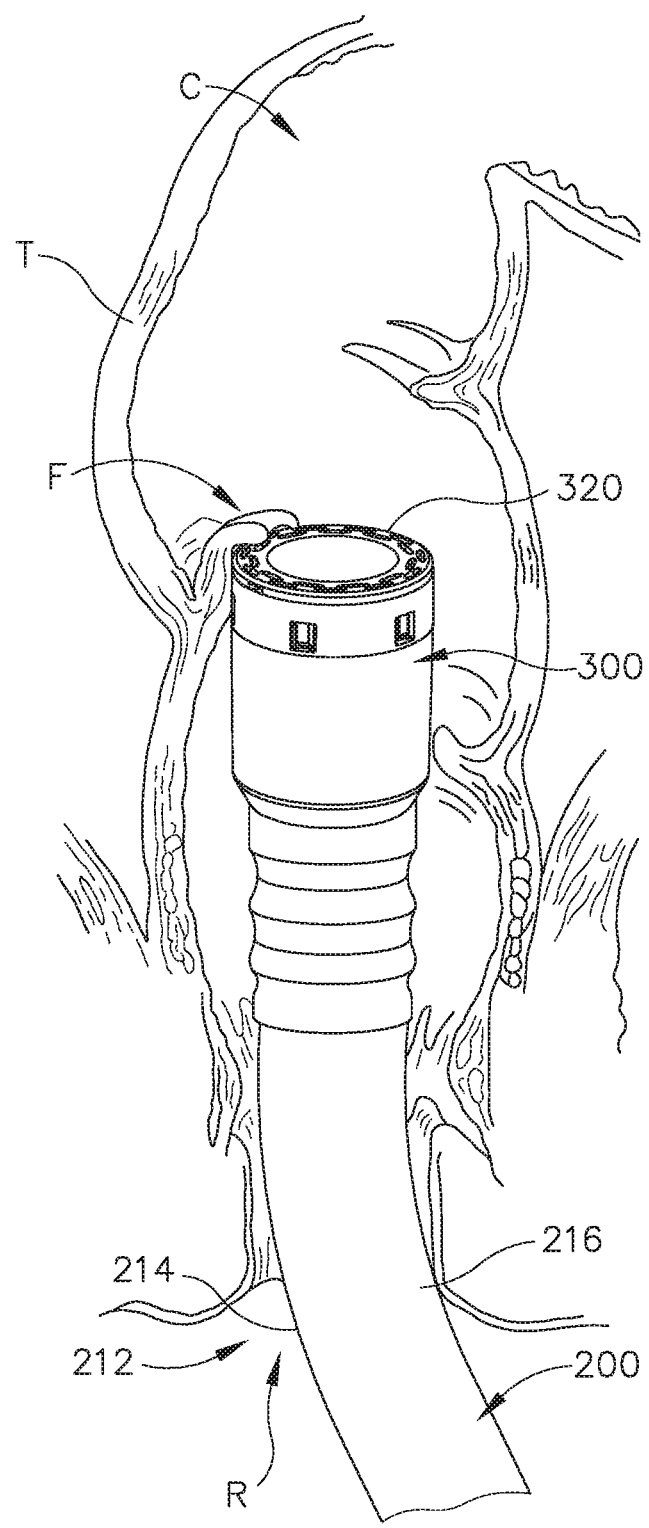
FIG. 9 depicts a partial perspective view of the stapling head assembly and shaft assembly of the circular stapler of FIG. 1 inserted in a patient's colon, with the stapling head assembly engaging a fold of the colon tissue, and with the patient's anatomy shown in cross-section.

Similarly, as shown in FIG. 9, those of ordinary skill in the art will recognize that the tissue (T) of the colon (C) defines a plurality of folds (F), and that stapling head assembly (300) may get snagged on such folds (F) as stapling head assembly (300) and shaft assembly (200) are inserted in the patient's colon (C). This snagging may also create a risk of damaging the tissue (T) of the patient's colon (C). Again, in versions where deck member (320) has tissue gripping features and/or other protruding features (e.g., staple guidance features, etc.), such features may increase the risk of damage to the tissue (T) of the patient's colon (C) as stapling head assembly (300) gets snagged on folds (F).

It may therefore be desirable to provide a version of stapling head assembly (300) that minimizes the risk of damaging the tissue (T) of the patient's colon (C) during insertion of stapling head assembly (300) and shaft assembly (200) into the patient's colon (C). Moreover, it may be desirable to provide a version of stapling head assembly (300) that includes features that enhance gripping of tissue during actuation of stapling head assembly (300), thereby promoting successful tissue cutting and staple deployment, without increasing the risk of damaging the tissue (T) of the patient's colon (C) during insertion of stapling head assembly (300) and shaft assembly (200) into the patient's colon (C).

A. Exemplary Deck Member with Flat Zone and Tissue Engagement Feature Zone

Figure 10:
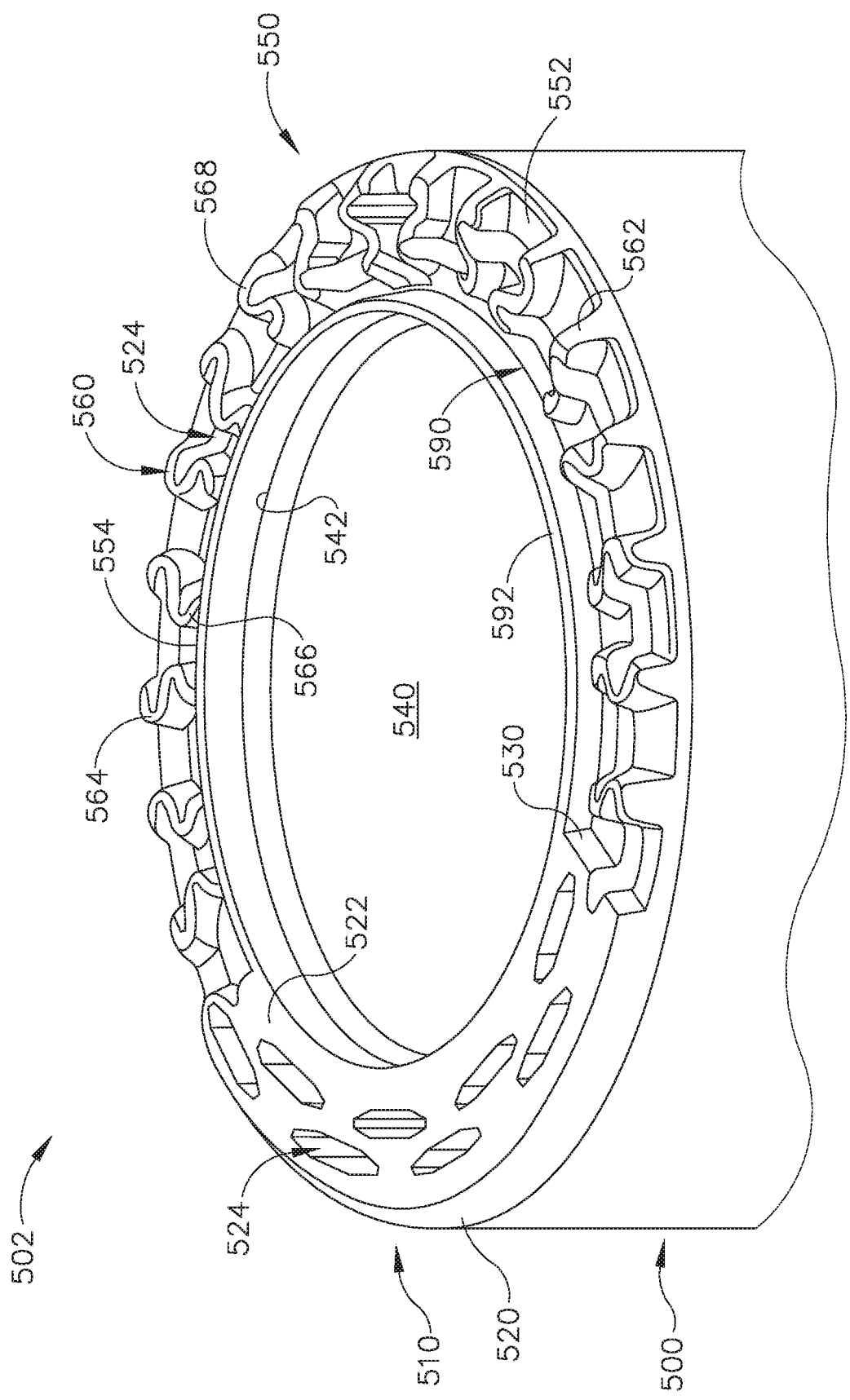
FIG. 10 depicts a perspective view of an exemplary alternative stapling head assembly that may be incorporated into the circular stapler of FIG. 1.

FIG. 10 shows an exemplary alternative stapling head assembly (500) that may be readily incorporated into stapling instrument in place of stapling head assembly (300). Except as otherwise described below, stapling head assembly (500) of this example is configured and operable just like stapling head assembly (300) described above. Stapling head assembly (500) of this example includes a deck member (502) having a deck surface (522) that defines two concentric annular arrays of staple openings (524). Staple openings (524) are arranged to correspond with the arrangement of staple drivers (352) and staple forming pockets (414) described above. Thus, each staple opening (524) is configured to provide a path for a corresponding staple driver (352) to drive a corresponding staple through deck member (502) and into a corresponding staple forming pocket (414) when stapling head assembly (500) is actuated. Deck member (502) defines an inner diameter that is just slightly larger than the outer diameter defined by knife member (540). Deck member (502) is thus configured to allow knife member (540) to translate distally to a point where cutting edge (542) is distal to deck surface (522).

Unlike deck member (320) described above, deck member (502) of the present example includes a first zone (510) and a second zone (550). First zone (510) is characterized in that deck surface (522) is substantially flat within first zone (510). First zone (510) includes an outer edge (520) that has a curved configuration. Outer edge (520) is thus configured to reduce the risk of outer edge (520) snagging on tissue (T) as stapling head assembly (500) is inserted into the patient's colon (C).

Second zone (550) is characterized in that second zone has a recessed deck surface (552) with a plurality of stand-off features (560) protruding upwardly from recessed deck surface (552). A stepped transition (530) is formed at the boundaries between zones (510, 550), thereby providing a step-down from deck surface (522) to recessed deck surface (552). In some versions, transition (530) is oriented perpendicularly relative to surfaces (522, 552), such that transition (530) provides a steep drop-off from deck surface (522) to recessed deck surface (552). In some other versions, transition (530) is oriented obliquely relative to surfaces (522, 552), such that transition (530) provides a sloped transition from deck surface (522) to recessed deck surface (552). Alternatively, transition (530) may have a curved configuration or any other suitable configuration.

Stand-off features (560) each include an outwardly facing surface (562), an outer wall portion (564), and an inner wall portion (566). Outwardly facing surfaces (562) are curved to complement the curved configuration of outer edge (520). Outwardly facing surfaces (562) are thus configured to reduce the risk of stand-off features (560) snagging on tissue (T) as stapling head assembly (500) is inserted into the patient's colon (C). Outer wall portions (564) are configured to wrap partially around the outer array of staple openings (524). Outer wall portions (564) are thus configured and positioned to provide guidance to staples (90) exiting the outer array of staple openings (524). Inner wall portions (564) are configured to wrap partially around the inner array of staple openings (524). Inner wall portions (564) are thus configured and positioned to provide guidance to staples (90) exiting the inner array of staple openings (524).

Since each inner wall portion (566) is contiguous with a corresponding outer wall portion (564), and since the inner array of staple openings (524) is angularly offset from the inner array of staple openings (524), each stand-off feature (560) generally has a zig-zag configuration. In the present example, the upper edges (568) of stand-off features (560) are located on the same plane as deck surface (522), such that upper edges (568) and deck surface (522) will contact tissue along the same plane. In other words, while recessed deck surface (552) is recessed relative to upper edges (568), deck surface (522) is not recessed relative to upper edges (568). In some other versions, at least a portion of upper edges (568) extends above or below the plane of deck surface (522).

It should also be understood that stand-off features (560) are discretely formed in the present example, such that gaps are located between each stand-off feature (560) and the adjacent stand-off features (560). In some other versions, stand-off features (560) are contiguous with each other.

Second zone (550) also includes an upwardly protruding annular wall (592). Annular wall (592) is flush with deck surface (522). Annular wall (592) is configured to compress a partially annular region of tissue against anvil (400), thereby providing assistance for edge (542) of knife member (540) to shear tissue. Annular wall (592) is contiguous and coplanar with the inner region of deck surface (522), such that annular wall (592) and deck surface cooperate to compress a fully annular region of tissue against anvil (400), providing even compression along a full circumference of a tissue region. An annular recess (590) is formed between annular wall (590) and stand-off features (560). In some other versions, inner wall portions (566) extend fully to annular wall (590), such that annular wall (590) is connected directly to stand-off features (560) via inner wall portions (566).

It should be understood that the protruding configuration of stand-off features (560) relative to recessed deck surface (552) will provide tissue engagement effects in second zone (550) that are not provided in first zone (510). In particular, when tissue is compressed between deck member (502) and anvil (400) as described above, portions of the compressed tissue will enter the recessed areas adjacent to stand-off features (560). By having some of the tissue enter these recessed areas, this may reduce the total pressure that would otherwise be applied to the tissue if the tissue were being compressed against a consistently flat deck surface like deck surface (322). By reducing the total pressure on the tissue, deck member (502) may reduce the risk of the tissue from becoming fractured by over-compression. In addition to reducing the total pressure on tissue, the entry of tissue portions in recessed areas adjacent to stand-off features (560) may provide a grip on the compressed tissue that is greater than the grip that could otherwise be achieved using a consistently flat deck surface like deck surface (322). The enhanced grip of tissue may promote cleaner cutting by knife member (540) and also promote more successful deployment of staples (90) in the tissue. Thus, the presence of stand-off features (560) may both reduce the risk of over-compression of tissue and promote greater success in cutting and stapling the tissue.

Figure 11:
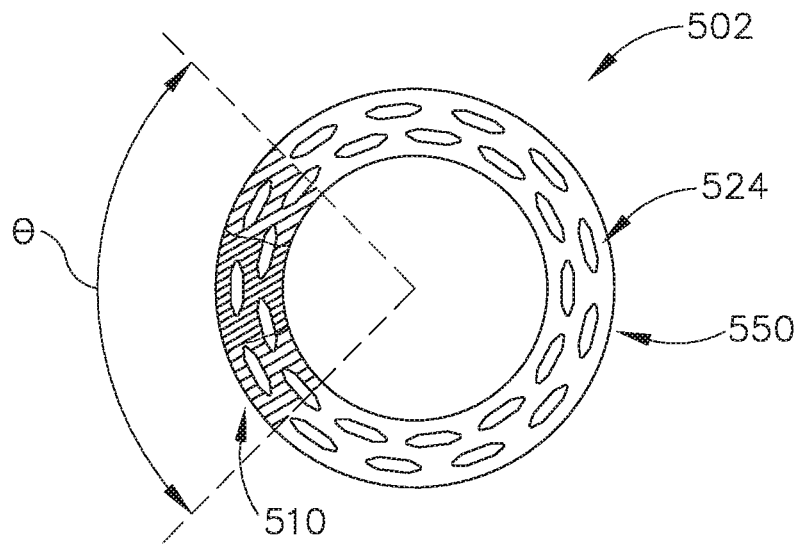
FIG. 11 depicts a top plan view of a deck member of the stapling head assembly of FIG. 10.

As best seen in FIG. 11, first zone (510) spans along an angular range (θ) of approximately 90° of the circumference of deck member (502) in the present example. By way of further example only, first zone (510) may span along an angular range (θ) of less than approximately 90° of the circumference of deck member (502). For instance, first zone (510) may span along an angular range (θ) between approximately 30° and approximately 90° of the circumference of deck member (502); or between approximately 45° and approximately 90° of the circumference of deck member (502).

As noted above, the entry of tissue into recessed areas adjacent to stand-off features (560) may reduce the risk of over-compression of tissue and promote greater success in cutting and stapling the tissue during actuation of anvil (400) and stapling head assembly (500). However, this same entry of tissue into recessed areas adjacent to stand-off features (560) may present some risks during insertion of stapling head assembly (500) and shaft assembly (200) into tissue. In other words, in variations of deck member (502) where stand-off features (560) are positioned along the full circumference of deck member (502), there may be a tendency for tissue (T) to enter the recessed areas adjacent to stand-off features (560) during insertion of shaft assembly (200) and a stapling head assembly (500) into the patient's colon (C). Any resulting snagging of tissue (T) on stand-off features (560) may increase the risk of damage to tissue (T) in the event that the tissue (T) is being pinched against the sacrum (S) as described above with reference to FIG. 8.

To avoid the above-noted risks that might otherwise be associated with tissue snagging on stand-off features (560) during insertion of shaft assembly (200) and stapling head assembly (500) into the patient's colon (C), first zone (510) is positioned to correspond with outer curve (214) of curved section (212) of shaft assembly (200). As shown in FIG. 8, the region of stapling head assembly (300) corresponding to outer curve (214) is the region of stapling head assembly (300) that would tend to pinch the tissue (T) against the sacrum (S). Thus, by having first zone (510) in this region, stapling head assembly (500) avoids the risks that might otherwise be associated with stand-off features (560) during insertion of shaft assembly (200) and stapling head assembly (500) into the patient's colon (C); while still providing the advantages of stand-off features (560) in second zone when anvil (400) and stapling head assembly (500) are actuated.

Figure 12:
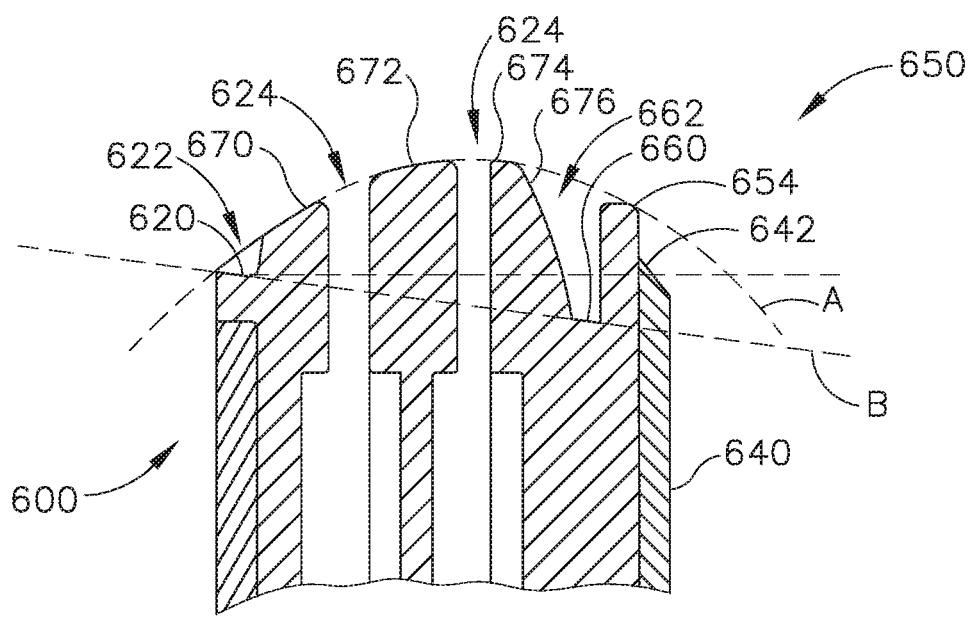
FIG. 12 depicts a partial cross-sectional view of another exemplary alternative stapling head assembly that may be incorporated into the circular stapler of FIG. 1.

FIG. 12 shows a portion of an exemplary alternative stapling head assembly (600), which comprises a cylindraceous knife member (640) and an alternative deck member (650). Stapling head assembly (600) is configured and operable just like stapling head assembly (500), except for the differences described below. In particular, the angular region of deck member (650) shown in FIG. 12 corresponds with second zone (550) of deck member (502). It should be understood that deck member (650) may have another angular region corresponding with first zone (510) of deck member (502) (i.e., with a flat deck surface like deck surface (520)). Alternatively, deck member (650) may be configured with the same geometry as represented in FIG. 12 about the full circumference of deck member (650). Of course, deck member (650) may have any other kinds of geometries and structural configurations along angular regions having any other arrangements and relationships with the angular region represented in FIG. 12.

Like deck member (502) described above, deck member (650) of the present example includes an inner annular array of staple openings (624) (shown as being closer to knife member (640)) and an outer annular array of staple openings (624) (shown as being further from knife member (640)). While only one inner staple opening (624) and one outer staple opening (624) are shown, it should be understood that additional staple openings (624) are provided in inner and outer annularly arrays that are angularly offset relative to each other, just like staple openings (524) of deck member (502).

FIG. 12 also shows a plurality of structural features adjacent to staple openings (624). In particular, a first radiused surface (670) is located outboard of outer staple opening (624). A second radiused surface (672) is located between outer and inner staple openings (624). A third radiused surface (674) is located inboard of inner staple opening (624). Radiused surfaces (670, 672, 674) all extend along the same curve (B) in this example. It should be understood that radiused surfaces (670, 672, 674) may be defined by a stand-off feature like stand-off feature (560) described above. In other words, stand-off feature (560) described above may be modified to provide radiused surfaces (670, 672, 674) of deck member (650), such that stand-off feature (560) has a generally concave cross-sectional profile along a transverse plane.

A recess (622) is formed outboard of first radiused surface (670), with an angled surface (620) providing the floor of recess (622). The angle of angled surface (620) is oriented along a line (B), which will be referred to again below.

Deck member (602) also includes an upwardly protruding annular wall (654), similar to annular wall (592) described above. Annular wall (654) extends to a height such that annular wall (654) distally terminates at a position along curve (B), described above. The distal termination point of annular wall (654) is also distal to cutting edge (642) of knife member (640). It should be understood that annular wall (654) is configured to compress a region of tissue against anvil (400), thereby providing assistance for edge (642) of knife member (640) to shear tissue. A recess (662) is formed outboard of annular wall (654), similar to recess (590) described above. While annular wall (654) provides one sidewall defining recess (662), a sharply sloped wall (676) provides another sidewall defining recess. Wall (676) is contiguous with third radiused surface (674) and provides a steeply sloped curved transition to an angled surface (660), which provides a floor of recess (662). The angle of angled surface (660) is oriented along the same line (B) as the angle of angled surface (620) described above.

As can be seen in FIG. 12, line (B) slopes downwardly from the outer diameter of stapling head assembly toward the inner diameter of stapling head assembly. As can also be seen in FIG. 12, due to the positioning and orientation of line (B), and due to the positioning and configuration of curve (A), recess (662) is substantially deeper than recess (622). Thus, to the extent that the depth of recesses (622, 620) is proportional to the tissue gripping enhancement provided by recesses (662, 660), recess (662) would provide greater tissue gripping than recess (622). Similarly, the manner in which the effective height of radiused surfaces (670, 672, 674) increases progressively toward the inner diameter of stapling head assembly will also provide increasingly greater tissue gripping toward the inner diameter of stapling head assembly. Conversely, the relatively shallow depth of recess (622), and the relatively short height of radiused surface (670), will provide minimized drag against tissue (T) as stapling head assembly (600) is advanced through the colon (C). The curved profile provided by radiused surfaces (670, 672, 674) may also assist in minimizing drag against tissue (T) as stapling head assembly (600) is advanced through the colon (C).

Figure 13:
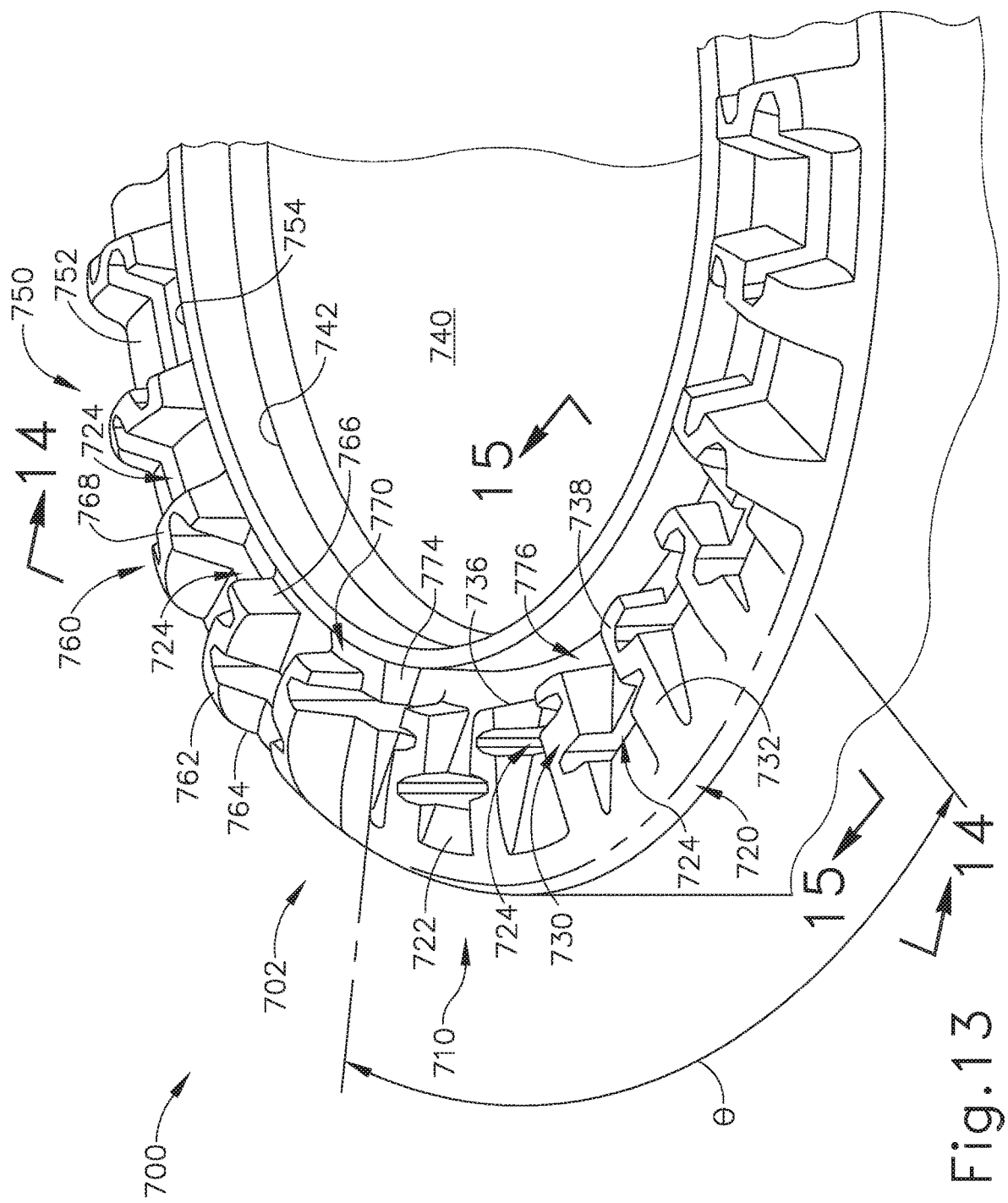
FIG. 13 depicts a partial perspective view of another exemplary alternative stapling head assembly that may be incorporated into the circular stapler of FIG. 1.

B. Exemplary Deck Member with Zones Having Differing Tissue Engagement Feature Aggressiveness FIG. 13 shows a portion of another exemplary alternative stapling head assembly (700), which comprises a cylindraceous knife member (740) and an alternative deck member (702). Stapling head assembly (700) is configured and operable just like stapling head assembly (500), except for the differences described below. Stapling head assembly (700) of this example includes a deck member (702) with an outer edge (720) that has a curved configuration. Outer edge (720) is thus configured to reduce the risk of outer edge (720) snagging on tissue (T) as stapling head assembly (700) is inserted into the patient's colon (C).

Deck member (702) also has deck surfaces (722, 752) that define two concentric annular arrays of staple openings (724). Staple openings (724) are arranged to correspond with the arrangement of staple drivers (352) and staple forming pockets (414) described above. Thus, each staple opening (724) is configured to provide a path for a corresponding staple driver (752) to drive a corresponding staple through deck member (700) and into a corresponding staple forming pocket (414) when stapling head assembly (700) is actuated. Deck member (702) of the present example also includes an inner annular wall (754), which protrudes upwardly relative to deck surfaces (722, 752). Annular wall (754) defines an inner diameter that is just slightly larger than the outer diameter defined by knife member (740). Deck member (702) is thus configured to allow knife member (740) to translate distally to a point where cutting edge (742) is distal to deck surfaces (722, 752) and annular wall (754). Annular wall (754) is configured to compress a partially annular region of tissue against anvil (400), thereby providing assistance for edge (742) of knife member (740) to shear tissue.

Like deck member (502) described above, deck member (702) of the present example includes a first zone (710) and a second zone (750). In some versions, first zone (710) spans along an angular range (θ) of approximately 45° of the circumference of deck member (702). By way of further example only, first zone (710) may span along an angular range (θ) of up to approximately 90° of the circumference of deck member (702). For instance, first zone (710) may span along an angular range (θ) between approximately 30° and approximately 90° of the circumference of deck member (702); or between approximately 45° and approximately 90° of the circumference of deck member (702).

Figure 15:
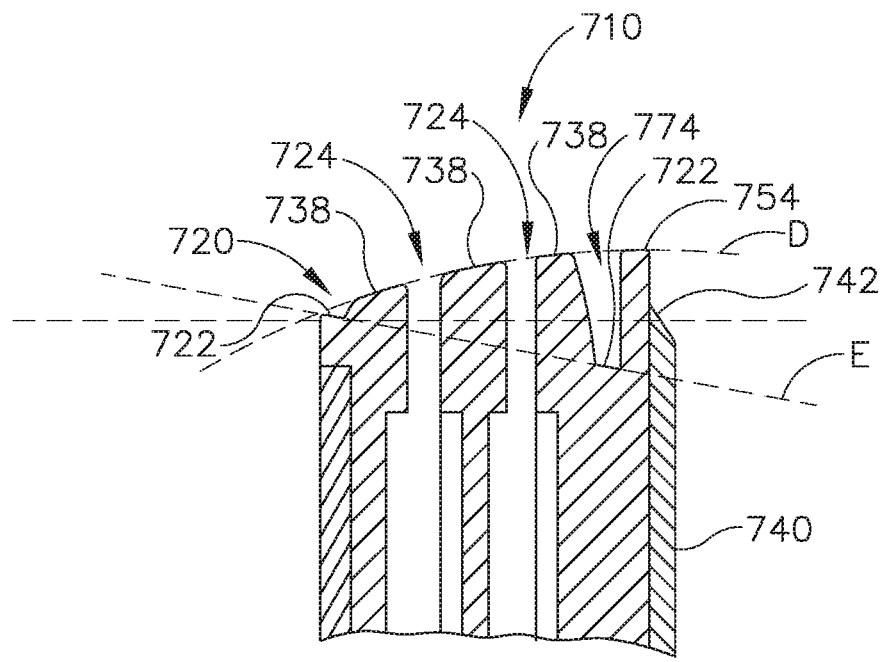
FIG. 15 depicts a partial cross-sectional view of the stapling head assembly of FIG. 13, taken along line 15-15 of FIG. 13.

First zone (710) includes deck surface (722), which is obliquely angled relative to the longitudinal axis of stapling head assembly (700). In particular, as shown in FIG. 15 and as described in greater detail below, deck surface (722) slopes downwardly or proximally from outer edge (720) to the radially innermost region of deck surface (722). In some other versions, deck surface (722) extends along a plane that is perpendicular to the longitudinal axis of stapling head assembly (700).

First zone (710) also includes a plurality of stand-off features (730) protruding upwardly from deck surface (722). Stand-off features (730) each include an outer wall portion (732) and an inner wall portion (736). Outer wall portions (732) are configured to wrap partially around the outer array of staple openings (724). Outer wall portions (732) are thus configured and positioned to provide guidance to staples (90) exiting the outer array of staple openings (724). Inner wall portions (736) are configured to wrap partially around the inner array of staple openings (724). Inner wall portions (734) are thus configured and positioned to provide guidance to staples (90) exiting the inner array of staple openings (724). An annular recess (776) is formed between annular wall (754) and stand-off features (730). In some other versions, inner wall portions (736) extend fully to annular wall (754), such that annular wall (754) is connected directly to stand-off features (730) via inner wall portions (736).

Since each inner wall portion (736) is contiguous with a corresponding outer wall portion (732), and since the inner array of staple openings (724) is angularly offset from the inner array of staple openings (724), each stand-off feature (730) generally has a zig-zag configuration. It should also be understood that stand-off features (730) are discretely formed in the present example, such that gaps are located between each stand-off feature (730) and the adjacent stand-off features (730). In some other versions, stand-off features (730) are contiguous with each other.

Figure 14:
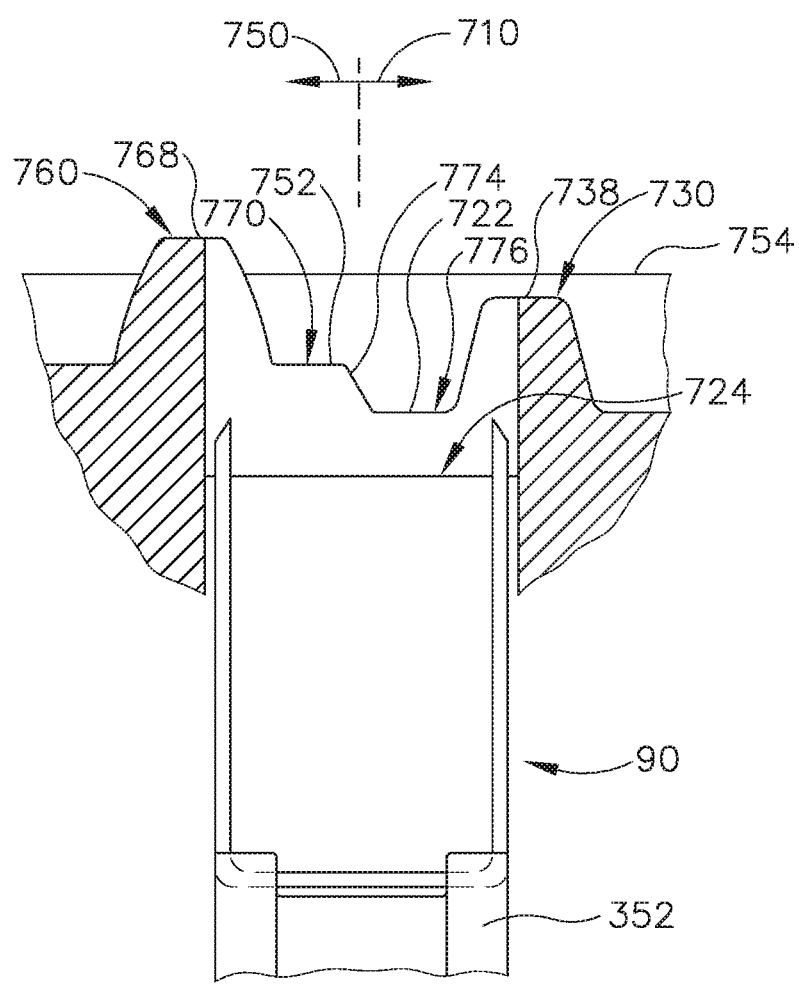
FIG. 14 depicts a partial cross-sectional view of the stapling head assembly of FIG. 13, taken along line 14-14 of FIG. 13.

In the version shown in FIGS. 13-14, the upper edges (768) of stand-off features (760) are located below the plane of the upper edge of annular wall (754), such that annular wall (754) will contact tissue just before upper edges (768) contact the tissue. In some other versions, as shown in FIG. 15, at least a portion of upper edges (768) are located along the same plane as the upper edge of annular wall (754), such that upper edges (768) and annular wall (754) will contact tissue along the same plane.

Regardless of the relationship between the height of upper edges (768) and the height of annular wall (754), it should be understood that upper edges (768) may have any suitable relationship with deck surface (752). For instance, in the version shown in FIG. 13, upper edges (738) of stand-off features (730) are located on the same plane as deck surface (752), such that upper edges (738) and deck surface (752) will contact tissue along the same plane. In other words, while deck surface (752) is recessed relative to upper edges (768) of stand-off features, deck surface (752) is not recessed relative to upper edges (738) of stand-off features (730). In some other versions, as shown in FIG. 14, at least a portion of upper edges (738) extends above the plane of deck surface (752). In still other versions, at least a portion of upper edges (738) extends below the plane of deck surface (752).

Second zone (750) also has a plurality of stand-off features (760) protruding upwardly from a deck surface (752). Unlike deck surface (722) of first zone (710), deck surface (752) of second zone (750) extends along a plane that is perpendicular to the longitudinal axis of stapling head assembly (700). As best seen in FIG. 14, there a sloped transition surface (774) provides a transition from deck surface (752) to deck surface (722), such that transition surfaces (774) defined the boundaries between first and second zones (710, 750). While each transition surface (774) is sloped in the present example, it should be understood that transition surface (774) may have any other suitable configuration. For instance, transition surface (774) may provide a steep step-down (e.g., like transition (530) described above), a curved transition, or any other suitable kind of transition.

Stand-off features (760) each include an outwardly facing surface (764), an outer wall portion (762), and an inner wall portion (766). Outwardly facing surfaces (764) are curved to complement the curved configuration of outer edge (720). Outwardly facing surfaces (762) are thus configured to reduce the risk of stand-off features (760) snagging on tissue (T) as stapling head assembly (700) is inserted into the patient's colon (C). Outer wall portions (762) are configured to wrap partially around the outer array of staple openings (724). Outer wall portions (762) are thus configured and positioned to provide guidance to staples (90) exiting the outer array of staple openings (724). Inner wall portions (766) are configured to wrap partially around the inner array of staple openings (724). Inner wall portions (764) are thus configured and positioned to provide guidance to staples (90) exiting the inner array of staple openings (724). An annular recess (770) is formed between annular wall (754) and stand-off features (760). In some other versions, inner wall portions (766) extend fully to annular wall (754), such that annular wall (754) is connected directly to stand-off features (760) via inner wall portions (766).

Since each inner wall portion (766) is contiguous with a corresponding outer wall portion (762), and since the inner array of staple openings (724) is angularly offset from the inner array of staple openings (724), each stand-off feature (760) generally has a zig-zag configuration. It should also be understood that stand-off features (760) are discretely formed in the present example, such that gaps are located between each stand-off feature (760) and the adjacent stand-off features (760). In some other versions, stand-off features (760) are contiguous with each other.

In the version shown in FIG. 13, the upper edges (768) of stand-off features (760) are located above the plane of the upper edge of annular wall (754), such that upper edges (768) will contact tissue just before annular wall (754) contacts the tissue. In some other versions, at least a portion of upper edges (768) are located along the same plane as the upper edge of annular wall (754), such that upper edges (768) and annular wall (754) will contact tissue along the same plane. In still other versions, at least a portion of upper edges (768) are located below the plane of annular wall (754), such that annular wall (754) will contact tissue just before upper edges (768) contact tissue.

FIG. 15 shows an exemplary cross-sectional profile that may be employed in first zone (710). In such versions, upper edges (768) in second zone (750) are located above the plane of the upper edge of annular wall (754). However, it should be understood that the cross-sectional profile shown in FIG.

15 may alternatively be employed in second zone (750). In such versions, upper edges (738) in first zone (710) are located below the plane of the upper edge of annular wall (754). In the present example, FIG. 15 shows how deck surface (722) is sloped downwardly from the outer region of deck member (702) toward the inner region of deck member (702), along line (E). FIG. 15 also shows how upper edge (738) of stand-off feature (730) and the upper edge of annular wall (754) all extend along the same curve (D). Of course, this configuration and set of relationships is just one merely illustrative example.

It should be understood that the protruding configuration of stand-off features (760) relative to deck surface (752) will provide tissue engagement effects similar to those described above in the context of deck member (502). In particular, when tissue is compressed between deck member (702) and anvil (400) as described above, portions of the compressed tissue will enter the recessed areas adjacent to stand-off features (760). By having some of the tissue enter these recessed areas, this may reduce the total pressure that would otherwise be applied to the tissue if the tissue were being compressed against a consistently flat deck surface like deck surface (322). By reducing the total pressure on the tissue, deck member (702) may reduce the risk of the tissue from becoming fractured by over-compression. In addition to reducing the total pressure on tissue, the entry of tissue portions in recessed areas adjacent to stand-off features (760) may provide a grip on the compressed tissue that is greater than the grip that could otherwise be achieved using a consistently flat deck surface like deck surface (322). The enhanced grip of tissue may promote cleaner cutting by knife member (740) and also promote more successful deployment of staples (90) in the tissue. Thus, the presence of stand-off features (760) may both reduce the risk of over-compression of tissue and promote greater success in cutting and stapling the tissue.

It should be understood that the above-described enhanced gripping and reduction of over-compression risk may also be provided in first zone (710). In particular, the protruding configuration of stand-off features (730) relative to deck surface (722) will provide some tissue engagement effects, though such effects may be less pronounced in first zone (710) than in second zone (750). When tissue is compressed between deck member (702) and anvil (400) as described above, portions of the compressed tissue will enter the recessed areas adjacent to stand-off features (730). This may reduce the total pressure that would otherwise be applied to the tissue if the tissue were being compressed against a consistently flat deck surface like deck surface (322); and may also provide a grip on the compressed tissue that is greater than the grip that could otherwise be achieved using a consistently flat deck surface like deck surface (322). Thus, the presence of stand-off features (730) in first zone (710) may both reduce the risk of over-compression of tissue and promote greater success in cutting and stapling the tissue, within first zone (710).

In versions of first zone (710) having a cross-sectional profile like the one shown in FIG. 15, it should be understood that the tissue engagement effects may be more pronounced at the inner region of first zone (710) than the tissue engagement effects at the outer region of first zone (710). In other words, due to the combination of structural features being positioned along downwardly sloped line (E) and structural features being positioned along curve (D), the tissue engagement effects of stand-off features (730) may progressively increase from the outermost region of first zone (710) to the innermost region of first zone (710).

As noted above, the entry of tissue into recessed areas adjacent to stand-off features (730, 760) may reduce the risk of over-compression of tissue and promote greater success in cutting and stapling the tissue during actuation of anvil (400) and stapling head assembly (700). However, this same entry of tissue into recessed areas adjacent to stand-off features (760) may present some risks during insertion of stapling head assembly (700) and shaft assembly (200) into tissue. In other words, in variations of deck member (702) where the full circumference of deck member (502) is configured like second zone (750) of deck member (702), there may be a tendency for tissue (T) to enter the recessed areas adjacent to stand-off features (760) during insertion of shaft assembly (200) and a stapling head assembly (700) into the patient's colon (C). Any resulting snagging of tissue (T) on stand-off features (760) may increase the risk of damage to tissue (T) in the event that the tissue (T) is being pinched against the sacrum (S) as described above with reference to FIG. 8.

To avoid the above-noted risks that might otherwise be associated with tissue snagging on stand-off features (760) during insertion of shaft assembly (200) and stapling head assembly (500) into the patient's colon (C), first zone (710) is positioned to correspond with outer curve (214) of curved section (212) of shaft assembly (200). As shown in FIG. 8, the region of stapling head assembly (300) corresponding to outer curve (214) is the region of stapling head assembly (300) that would tend to pinch the tissue (T) against the sacrum (S). It should be understood that the reduced effective height of stand-off features (730) relative to stand-off features (760) may result in stand-off features (730) presenting a lower risk of stand-off features (730) pinching tissue (T) against the sacrum (S), as compared to the risk of such pinching presented by stand-Off features (760).

Thus, by having first zone (710) in the region of stapling head assembly (300) that would tend to pinch the tissue (T) against the sacrum (S), stapling head assembly (700) avoids the risks that might otherwise be associated with stand-off features (760) during insertion of shaft assembly (200) and stapling head assembly (700) into the patient's colon (C); while still providing the advantages of stand-off features (760) in second zone when anvil (400) and stapling head assembly (700) are actuated. Moreover, the presence of stand-off features (730) within first zone (710) may still provide some of the same tissue engagement benefits that are provided by stand-off features (760), though to a somewhat lesser degree than the tissue engagement benefits that are provided by stand-off features (760).

Figure 16:
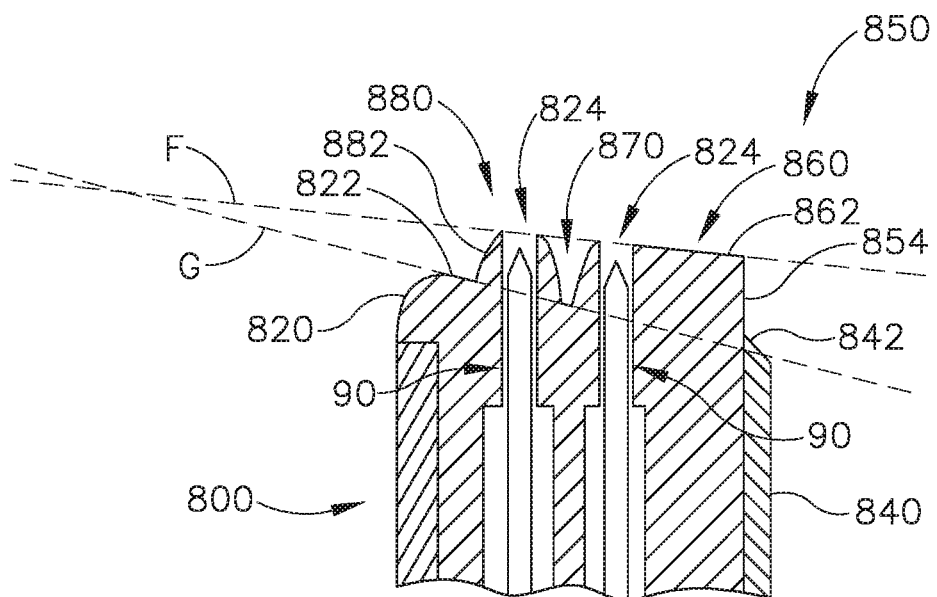
FIG. 16 depicts a partial cross-sectional view of another exemplary alternative stapling head assembly that may be incorporated into the circular stapler of FIG. 1.

C. Exemplary Deck Member with Combination of Connected and Non-Connected Tissue Engagement Features FIG. 16 shows a portion of an exemplary alternative stapling head assembly (800), which comprises a cylindraceous knife member (840) and an alternative deck member (850). Stapling head assembly (800) is configured and operable just like stapling head assembly (500, 600, 700), except for the differences described below. In some versions, the angular region of deck member (850) shown in FIG. 16 corresponds with only one portion of the full angular range of deck member (850). In some other versions, the angular region of deck member (850) shown in FIG. 16 corresponds with the full angular range of deck member (850). Of course, deck member (850) may have any other kinds of geometries and structural configurations along angular regions having any other arrangements and relationships with the angular region represented in FIG. 16.

Like deck member (502, 650, 702) described above, deck member (850) of the present example includes an inner annular array of staple openings (824) (shown as being closer to knife member (840)) and an outer annular array of staple openings (824) (shown as being further from knife member (840)). While only one inner staple opening (824) and one outer staple opening (824) are shown, it should be understood that additional staple openings (824) are provided in inner and outer annularly arrays that are angularly offset relative to each other, just like staple openings (524, 724) of deck member (502, 702).

FIG. 16 also shows a first stand-off feature (880) surrounding the outermost staple opening (824) and a second stand-off feature (860) surrounding the innermost staple opening (824). First stand-off feature (880) includes a curved outer wall (882) that inwardly and outwardly terminates at deck surface (822). Deck surface (822) outwardly terminates at a curved outer edge (820). A recess (870) is defined inboard of first stand-off feature (880), with deck surface (822) defining a sloped floor of recess (870). In particular, the regions of deck surface (822) that are inboard and outboard of first stand-off feature (880) are oriented along a line (G), which slopes downwardly from the outer region of deck member (802) toward the inner region of deck member (802). In some other versions, this line (G) is oriented perpendicularly relative to the longitudinal axis of stapling head assembly (800). In still other versions, this line (G) slopes upwardly from the outer region of deck member (802) toward the inner region of deck member (802).

Second stand-off feature (860) includes an inclined upper surface (862) that outwardly terminates at deck surface (822) in recess (870). Upper surface (862) inwardly terminates at inner wall (854) of deck member (802). While not shown, it should be understood that deck member (802) may also include a separate annular wall like annular walls (592, 654, 754) described above, which may extend along the angular regions of deck member (802) where second stand-off features (860) are angularly spaced apart from each other. In other words, stand-off features (860) may be discretely positioned in an angularly spaced array, with stand-off features (860) being integral with an annular wall that extends between the discrete stand-off features (860).

As shown in FIG. 16, the upper edge (824) of first stand-off feature (880) and upper surface (862) of second stand-off feature (860) extend along the same plane, indicated by line (F). This line (F) slopes downwardly from the outer region of deck member (802) toward the inner region of deck member (802). In the present example, the slope of line (G) is steeper than the slope of line (F), though this relationship may be reversed in some other versions. It should be understood that the relative orientations of lines (F, G) in this example results in second stand-off feature (860) having a greater effective height than the effective height of first stand-off feature (880). In some other versions, first stand-off feature (880) has a greater effective height than the effective height of second stand-off feature (860).

It should be understood that the combination of stand-off features (860, 880) and recess (870) may provide tissue engagement effects similar to those described above. In particular, the combination of stand-off features (860, 880) and recess (870) may provide enhanced gripping of tissue by deck member (802) while also providing a reduced pressure profile against tissue that is compressed between anvil (400) and deck member (802). To the extent that second stand-off features (860) have a greater effective height than the effective height of first stand-off features (880), the tissue engagement effects may be more pronounced toward the inner region of deck member (802) as compared to the tissue engagement effects provided at the inner region of deck member (802).

It should also be understood that deck member (802) may include a zone where stand-off features (860, 880) are omitted or at least less pronounced. Having such a zone may reduce the risk of deck member (802) snagging against tissue (T) as stapling head assembly (800) is being inserted into the patient's colon. Similarly, having such a zone may reduce the risk of deck member (802) damaging tissue (T) by pinching the tissue (T) against the sacrum (S) as stapling head assembly (800) is being inserted into the patient's colon (C). In such versions having a "no-snag" zone, the "no-snag" zone may be positioned to correspond with outer curve (214) of curved section (212) of shaft assembly (200).

D. Exemplary Deck Member with Tissue Engagement Features to Limit Tissue Flow

In some instances when tissue is being compressed between anvil (400) and deck member (320), the tissue may tend to migrate or "flow," in inward and/or outward radial directions, from the space between anvil (400) and deck member (320). In addition, or in the alternative, in some instances when tissue is being compressed between anvil (400) and deck member (320), the tissue may tend to migrate or flow in a twisting fashion, about the longitudinal axis of stapling head assembly (300) and anvil (400). It may therefore be desirable to provide a modified version of deck member (320) with tissue engagement features that prevent or otherwise control the migration or flow of tissue in radial and angular directions.

Figure 17:
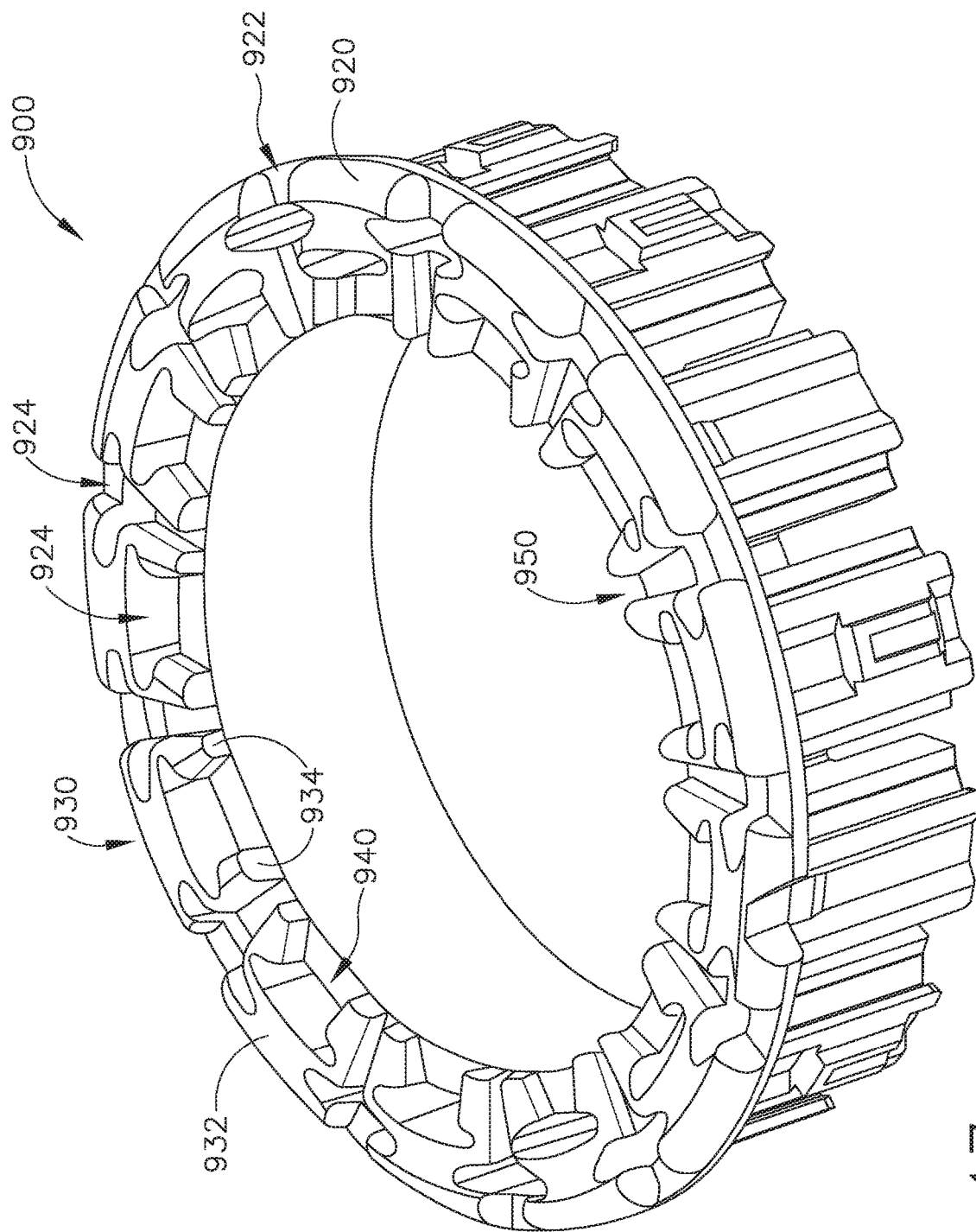
FIG. 17 depicts a perspective view of another exemplary alternative deck member that may be incorporated into the stapling head assembly of FIG. 4.

FIG. 17 shows an exemplary alternative deck member (900) that may be incorporated into stapling head assembly (300) in place of deck member (320). Deck member (900) of this example includes a deck surface (922) that defines an inner annular array of staple openings (924) and an outer annular array of staple openings (924). Deck member (900) further includes an angularly spaced array of stand-off features (930). Stand-off features (930) are angularly spaced in an array about the full circumference of deck member (900) in this example. A corresponding angularly spaced array of radially extending channels (950) are formed between stand-off features (930). Channels (950) are tapered such that channels (950) have a larger angular width at the radially outer region of deck member (900) than the angular width of channels (950) at the radially inner region of channels (950). Channels (950) pass over the outer array of staple openings (924), such that each channel (950) is associated with a corresponding staple opening (924). It should be understood that some alternative versions of deck member (900) may include a zone where stand-off features (930) are omitted or less pronounced, etc.

Each stand-off feature (930) includes an angularly extending outer portion (932) and a set of radially extending inner portions (934). Each outer portion (932) includes a curved outer edge (920). Each outer portion (932) also partially surrounds the angularly outermost ends of adjacent staple openings (924). In particular, each outer portion (932) partially surrounds just one end of a corresponding first staple opening (924) while also partially surrounding just one end of a corresponding second staple opening (924). Thus, a single outer portion (932) does not surround both ends of the same staple opening (924).

By contrast, each set of inner portions (934) for each stand-off feature (930) partially surrounds both of the angularly outermost ends of adjacent staple openings (924). Inner portions (934) are tapered in this example, such that the inner portions (934) of each stand-off feature (930) define a corresponding tapered recess (940). Each recess (940) leads to a corresponding staple opening (924) in the inner array of staple openings (924). Recesses (940) are tapered such that each recess (940) has a larger angular width at the radially inner region of deck member (900) than the angular width of recess (940) at the correspond staple opening (924).

It should be understood that stand-off features (930) may provide tissue engagement features similar to those described above. In particular, the combination of stand-off features (930), channels (950), and recesses (940) may provide enhanced gripping of tissue by deck member (900) while also providing a reduced pressure profile against tissue that is compressed between anvil (400) and deck member (900). Moreover, the configuration of channels (950) and recesses (940) may minimize or otherwise control the migration or flow of tissue in inward and/or outward radial directions, from the space between anvil (400) and deck member (900), as the tissue is being compressed between anvil (400) and deck member (900). Similarly, the configuration of channels (950) and recesses (940) may prevent the migration or flow of tissue in a twisting fashion, about the longitudinal axis of stapling head assembly (300) and anvil (400), as the tissue is being compressed between anvil (400) and deck member (900).

Figure 18:
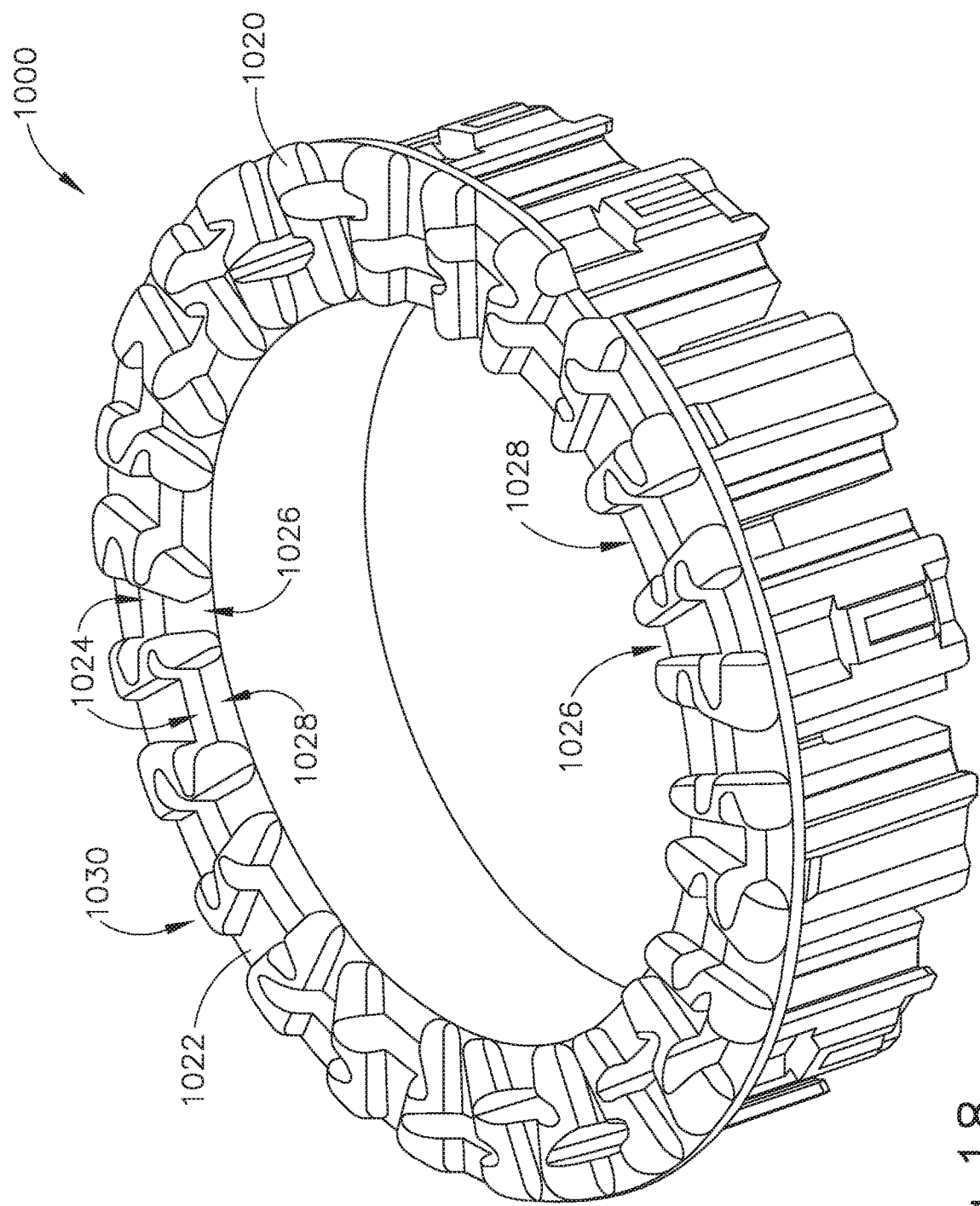
FIG. 18 depicts a perspective view of another exemplary alternative deck member that may be incorporated into the stapling head assembly of FIG. 4.

FIG. 18 shows another exemplary alternative deck member (1000) that may be incorporated into stapling head assembly (300) in place of deck member (320). Deck member (1000) of this example includes a deck surface (1022) that defines an inner annular array of staple openings (1024) and an outer annular array of staple openings (1024). Deck member (1000) further includes an angularly spaced array of stand-off features (1030). Stand-off features (1030) are angularly spaced in an array about the full circumference of deck member (1000) in this example. Each stand-off feature (1030) partially surrounds the end of one staple opening (1024) from the inner array of staple openings (1024) and one staple opening (1024) from the outer array of staple openings (1024). Each stand-off feature (1030) also includes a curved outer end (1020). It should be understood that some alternative versions of deck member (1000) may include a zone where stand-off features (1030) are omitted or less pronounced, etc.

An angularly spaced array of radially extending first channels (1026) and an angularly spaced array of radially extending second channels (1028) are formed between stand-off features (1030). Channels (1026) are angularly interposed between channels (1028), such that channels (1026, 1028) are arrayed in an alternating fashion. Channels (1026) are tapered such that each channel (1026) has a smaller angular width at the radially inner region of deck member (1000) than the angular width of channel (1026) at the radially outer region of deck member (1000). By contrast, channels (1028) are tapered such that each channel (1028) has a larger angular width at the radially inner region of deck member (1000) than the angular width of channel (1028) at the radially outer region of deck member (1000).

It should be understood that stand-off features (1030) may provide tissue engagement features similar to those described above. In particular, the combination of stand-off features (930) and channels (1026, 1028) may provide enhanced gripping of tissue by deck member (1000) while also providing a reduced pressure profile against tissue that is compressed between anvil (400) and deck member (1000). Moreover, the configuration of channels (1026, 1028) may minimize or otherwise control the migration or flow of tissue in inward and/or outward radial directions, from the space between anvil (400) and deck member (1000), as the tissue is being compressed between anvil (400) and deck member (1000). Similarly, the configuration of channels (1026, 1028) may prevent the migration or flow of tissue in a twisting fashion, about the longitudinal axis of stapling head assembly (300) and anvil (400), as the tissue is being compressed between anvil (400) and deck member (1000).

E. Exemplary Deck Member with Tissue Engagement Recesses

Figure 19:
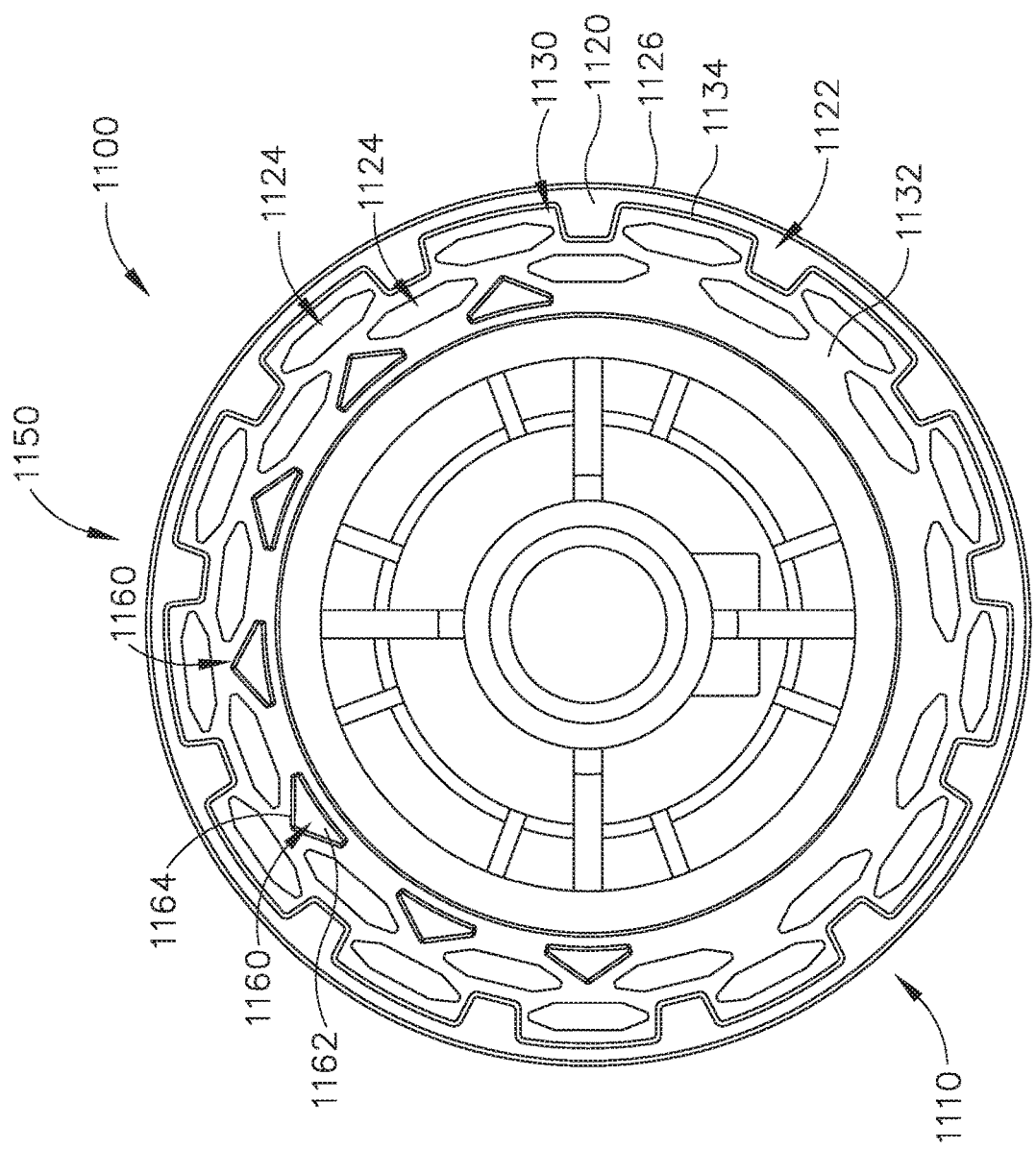
FIG. 19 depicts a top plan view of another exemplary alternative stapling head assembly that may be incorporated into the circular stapler of FIG. 1.
Figure 20:
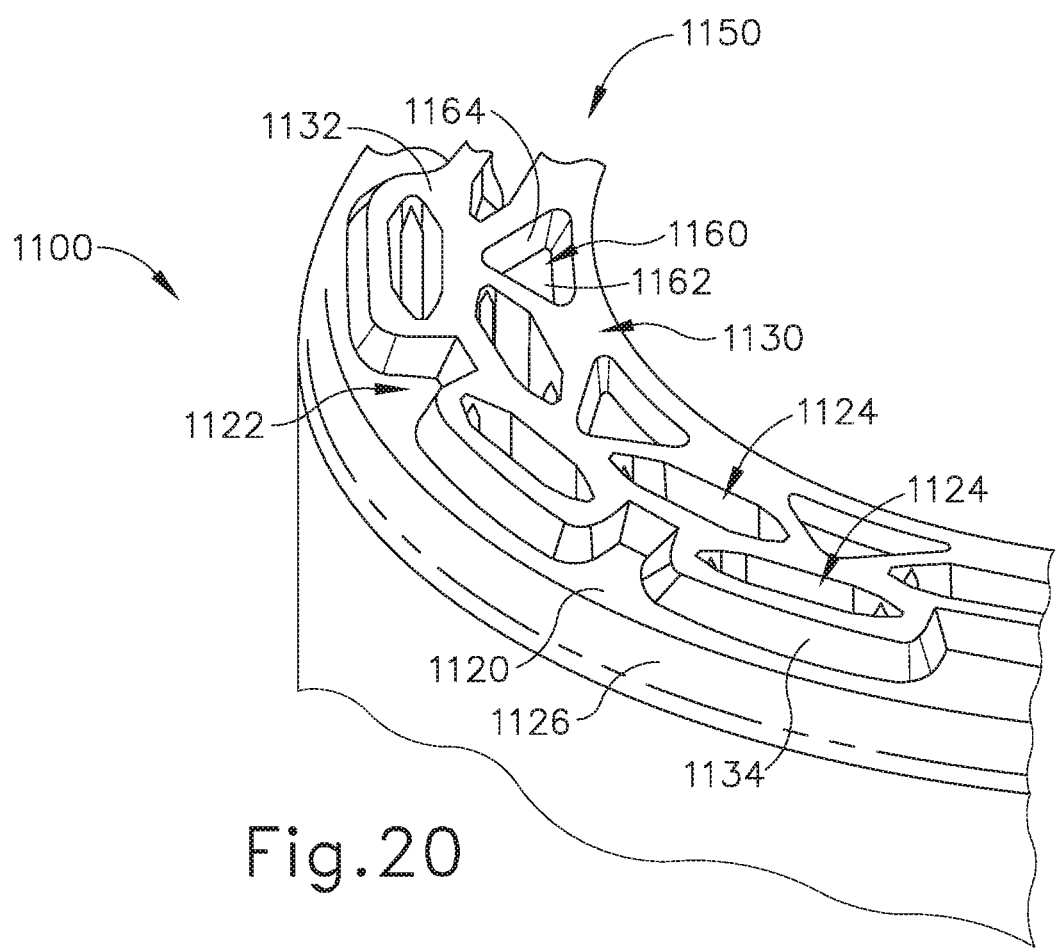
FIG. 20 depicts a partial perspective view of the stapling head assembly of FIG. 19.

FIGS. 19-20 show another exemplary alternative deck member (1100) that may be readily incorporated into stapling head assembly (300) in place of deck member (320). Deck member (1100) of this example is configured and operable just like deck member (320) except as otherwise described below. Deck member (1100) of the present example comprises an inner annular array of staple openings (1124) and an outer annular array of staple openings (1124). Deck member (1124) further includes a first deck surface (1120), a second deck surface (1132), and a curved outer edge (1126). Staple openings (1124) are formed through second deck surface (1132), with first deck surface (1120) being located outboard of second deck surface (1132).

As best seen in FIG. 20, second deck surface (1132) is proud relative to first deck surface (1120), such that first deck surface (1120) is recessed relative to second deck surface (1132). Portions of first deck surface (1120) extend inwardly relative in the spaces between the outer array of staple openings (1124), thereby effectively forming recesses (1122) between staple openings (1124) of the outer array of staple openings (1124). In the present example, deck member (1100) further provides angled transition surfaces (1134) between surfaces (1120, 1132). In the present example, transition surfaces (1134) are flat and obliquely angled relative to surfaces (1120, 1132), thereby providing a sloped transition between surfaces (1120, 1132). In some other versions, transition surfaces (1134) are curved. In some other versions, transition surfaces (1134) are perpendicular to surfaces (1120, 1132), thereby providing a steep step-down transition between surfaces (1120, 1132).

Figure 21:
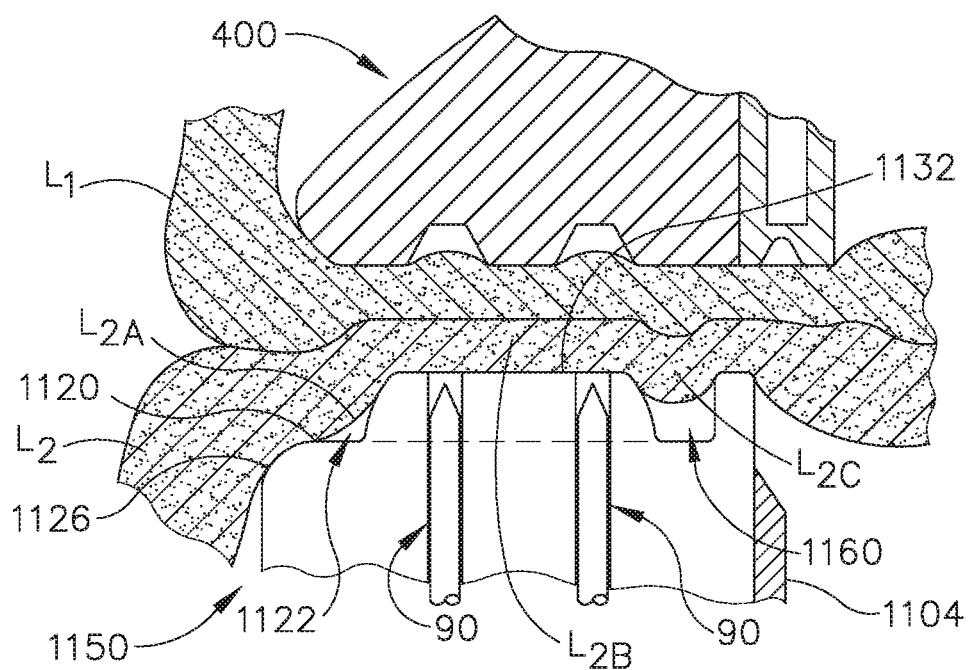
FIG. 21 depicts a partial cross-sectional view of an exemplary anvil compressing tissue against the stapling head assembly of FIG. 19.

Deck member (1100) of the present example further includes a set of triangular recesses (1160) formed in second deck surface (1132). Each triangular recess (1160) includes a floor (1162) and three angled sidewalls (1164) providing a transition from deck surface (1132) to floor (1162). In the present example, sidewalls (1164) are obliquely angled relative to surface (1132) and floor (1162), thereby providing a sloped transition from surface (1132) to floor (1162). In some other versions, sidewalls (1164) are curved. In some other versions, sidewalls (1164) are perpendicular to surface (1132) and floor (1162), thereby providing a steep step-down transition from surface (1132) to floor (1162). In the present example, and as best seen in FIG. 21, floor (1162) is located on the same plane as first deck surface (1120). In some other versions, floor (1162) is either higher or lower than first deck surface (1120).

As best seen in FIG. 19, triangular recesses (1160) are configured and positioned such that the outermost point of each triangular recess is located between corresponding staple openings (1124) of the inner array of staple openings (1124). As also shown in FIG. 19, deck member (1100) of the present example provides a first zone (1110) extending along a first angular range of deck member (1100) and a second zone (1150) extending along a second angular range of deck member (1100). Triangular recesses (1160) are included in second zone (1150) but not in first zone (1110). In some other variations, triangular recesses (1160) are arrayed along the full angular extent of deck member (1000), such that there are no different zones (1110, 1150).

FIG. 21 shows how recesses (1122, 1160) provide engagement effects on tissue ($L_1$, $L_2$) that is being compressed between anvil (400) and deck member (1100) within second zone (1150). In this depiction, an upper layer of tissue ($L_1$) is adjacent to anvil (400) while a lower layer of tissue ($L_2$) is adjacent to deck member (1100), with both layers of tissue ($L_1$, $L_2$) also being adjacent to each other. As shown, a radially outermost region of tissue ($L_{2A}$) enters recess (1122), a radially innermost region of tissue ($L_{2C}$) enters triangular recess (1160), and an intermediate region of tissue ($L_{2B}$) is fully compressed against second deck surface (1132). In other words, the compression of regions of tissue ($L_{2A}$, $L_{2C}$) is less than the compression of region of tissue ($L_{2B}$). It should be understood that the entry of regions of tissue ($L_{2A}$, $L_{2C}$) may reduce the overall pressure applied to tissue ($L_1$, $L_2$); and/or may provide an enhanced gripping effect on tissue ($L_1$, $L_2$).

It should be understood from the foregoing that recesses (1122, 1160) may provide tissue engagement effects that are similar to the tissue engagement effects described above as being provided by various kinds of stand-off features. Moreover, by relying on recesses rather than stand-offs to provide such tissue engagement effects, deck member (1100) may provide a further reduced risk of snagging tissue (T) during insertion of stapling head assembly (300) into the patient's colon (C).

F. Exemplary Deck Member Providing Variable Staple Height

Figure 22:
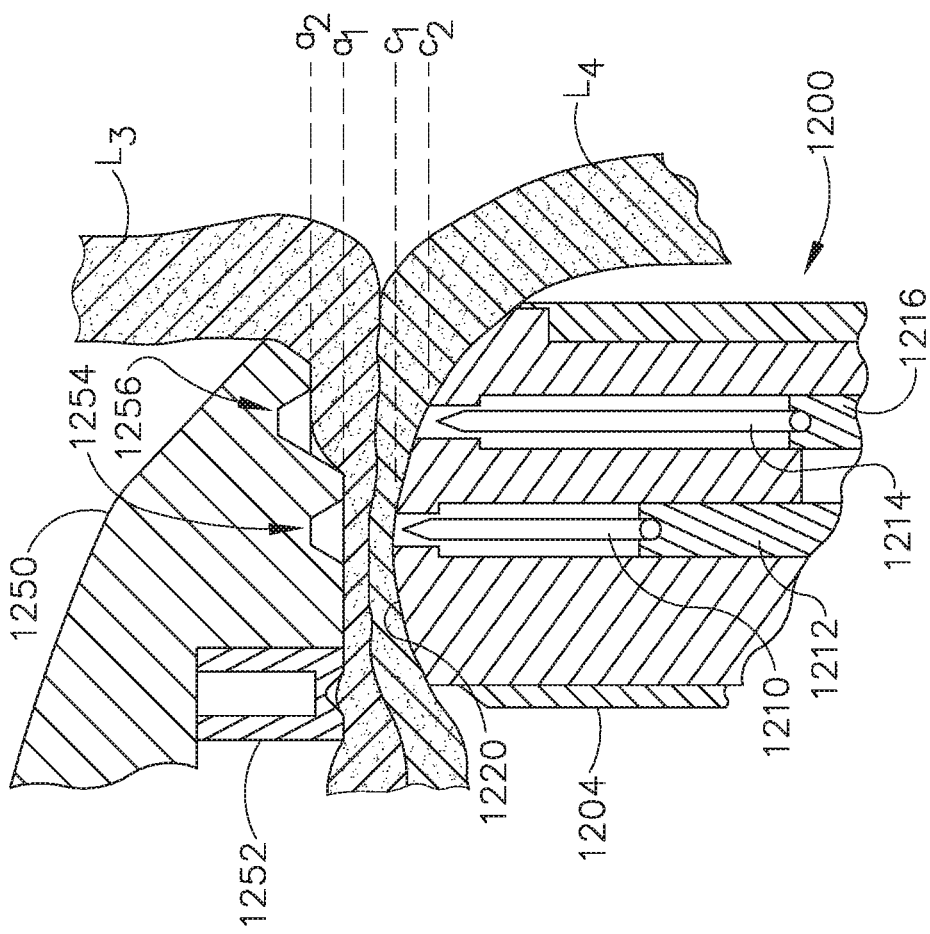
FIG. 22 depicts a partial cross-sectional view of an exemplary alternative anvil compressing tissue against an exemplary alternative stapling head assembly that may be incorporated into the circular stapler of FIG. 1.

FIG. 22 shows another exemplary stapling head assembly (1200) that may be readily incorporated into instrument (10) in place of stapling head assembly (300). FIG. 22 also shows another exemplary anvil (1250) that may be used in place of anvil (400). Stapling head assembly (1200) and anvil (1250) are substantially identical to stapling head assembly (300) and anvil (400) described above, respectively, except for the differences described below. Stapling head assembly (1200) of the present example comprises pair of staples (1210, 1214) with corresponding staple drivers (1212, 1216); a curved deck surface (1220); and a knife member (1204). In this example, staple (1214) has a greater height than staple (1210), and staple drivers (1212, 1216) are positioned and configured to account for these differences in staple heights. It should be understood that stapling head assembly (1200) includes an inner annular array of angularly spaced staples (1210) and corresponding staple drivers (1212); and an outer annular array of angularly spaced staples (1214) and corresponding staple drivers (1216).

The curvature of deck surface (1220) is contoured and positioned such that the outer region of deck surface (1220) is at a lower or more proximal location than the inner region of deck surface (1220). Due to this curvature, staple (1210) will exit deck surface (1220) at a point ($c_1$) that is distal to the point ($c_2$) at which staple (1214) will exit deck surface (1220). Also, the curvature of deck surface (1220) will provide variable pressure to the layers of tissue ($L_3$, $L_4$) compressed between deck surface (1220) and anvil (1250). Moreover, due to the curvature of deck surface (1220), deck surface (1220) will tend to squeeze the layers of tissue ($L_3$, $L_4$) radially outwardly as the layers of tissue ($L_3$, $L_4$) are compressed between deck surface (1220) and anvil (1250).

Anvil (1250) of the present example comprises a pair of staple forming pockets (1254, 1256). Staple forming pocket (1254) is positioned to correspond with staple (1210) while staple forming pocket (1214) is positioned to correspond with staple (1214). Staple forming pocket (1254) is located at a position ($a_1$) that is proximal relative to the position ($a_2$) at which staple forming pocket (1256) is located. Anvil (1250) also includes a breakable washer (1252), which is similar to breakable washer (417) as described above. In particular, washer (1252) is broken by knife member (1204) when knife member (1204) completes a full distal range of motion upon actuation of stapling head assembly (1200).

Figure 23:
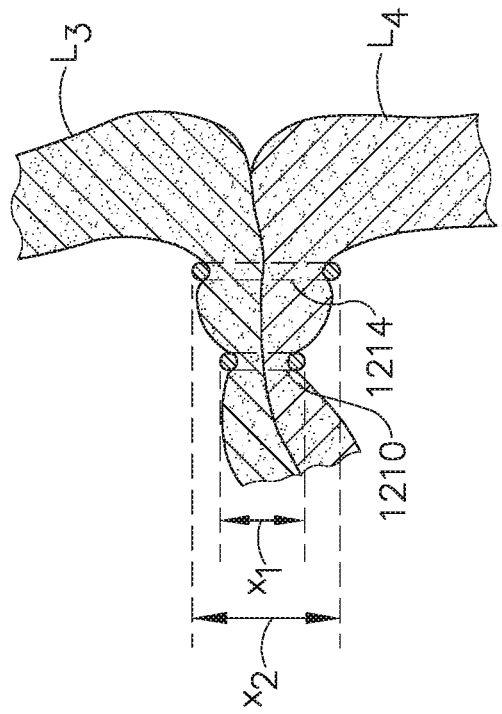
FIG. 23 depicts a cross-sectional view of the tissue of FIG. 22 after the stapling head assembly of FIG. 22 has been actuated and removed with the anvil of FIG. 22, leaving behind the tissue in a severed and stapled state.

FIG. 23 shows layers of tissue ($L_3$, $L_4$) after stapling head assembly (1200) has been actuated to sever and staple the tissue ($L_3$, $L_4$). In particular, FIG. 23 shows staple (1210) deployed in an inner region of tissue ($L_3$, $L_4$), with staple (1214) being deployed in an outer region of tissue ($L_3$, $L_4$). The deployed staple (1210) has a height ($x_1$) that is shorter than the height ($x_2$) of deployed staple (1214). This is due to the fact that unformed staple (1210) was shorter than unformed staple (1214), the exit point ($c_1$) of staple (1210) is distal in relation to the exit point ($c_2$) of staple (1214), and the position ($a_1$) of staple forming pocket (1254) is proximal in relation to the position ($a_2$) of staple forming pocket (1256). It should be understood that, by providing these varied heights ($x_1$, $x_2$), deployed staples (1210, 1214) may maintain the varied pressure profile that was applied against layers of tissue ($L_3$, $L_4$) by curved deck surface (1220) and the corresponding surface of anvil (1250).

Figure 24:
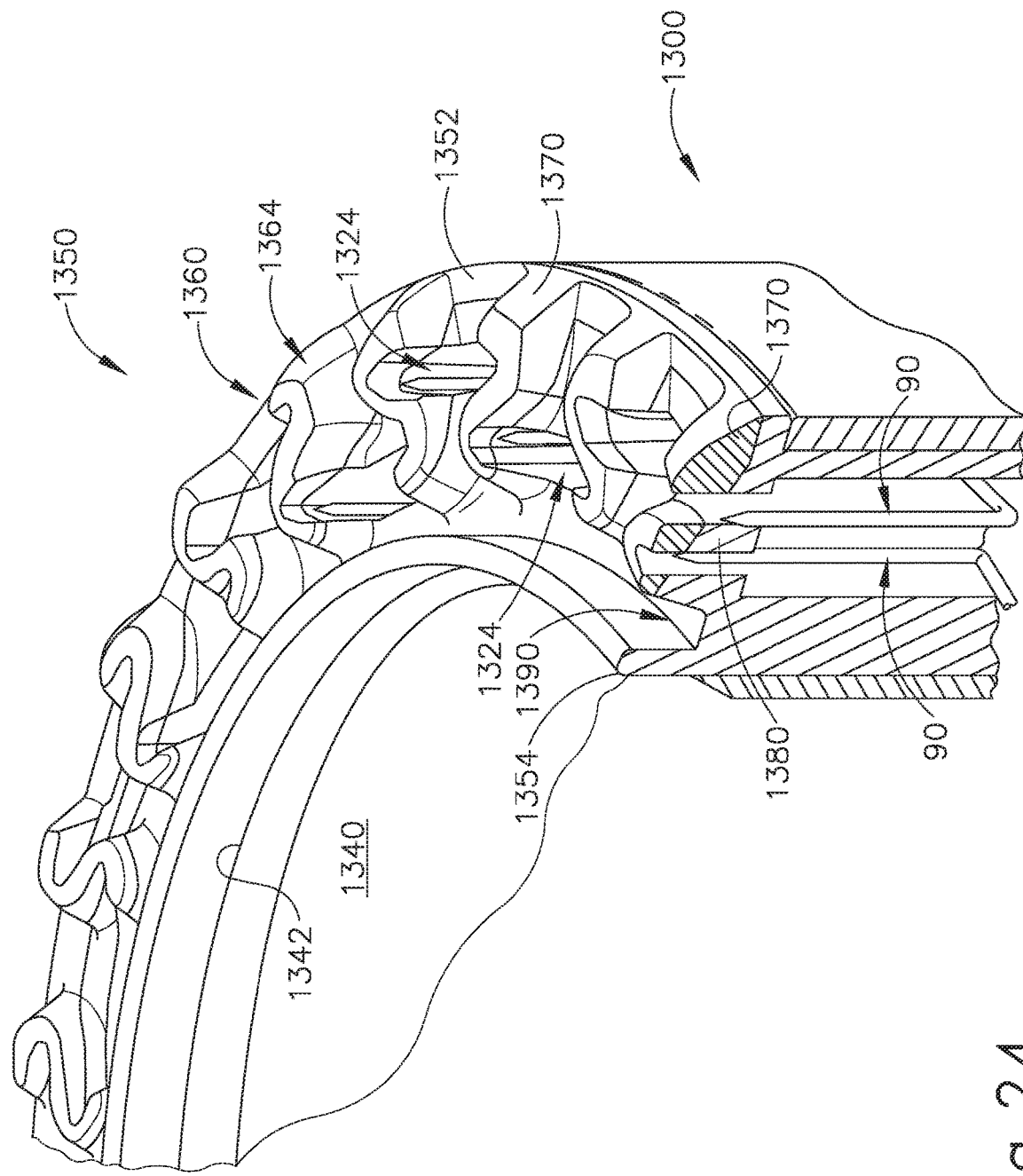
FIG. 24 depicts a partial perspective view of another exemplary alternative stapling head assembly that may be incorporated into the circular stapler of FIG. 1.

G. Exemplary Staple Deck Member with Combination of Rigid and Elastomeric Features FIGS. 24-26 show another exemplary stapling head assembly (1300) that may be readily incorporated into instrument (10) in place of stapling head assembly (300). Stapling head assembly (1300) is substantially identical to stapling head assembly (500) described above, except for the differences described below. Stapling head assembly (1300) of the present example comprises a deck member (1350) having a deck surface (1352) that defines two concentric annular arrays of staple openings (1324). Staple openings (1324) are arranged to correspond with the arrangement of staple drivers (352) and staple forming pockets (414) described above. Thus, each staple opening (1324) is configured to provide a path for a corresponding staple driver (352) to drive a corresponding staple (90) through deck member (1350) and into a corresponding staple forming pocket (414) when stapling head assembly (1300) is actuated. Deck member (1350) defines an inner diameter that is just slightly larger than the outer diameter defined by knife member (1340). Deck member (1350) is thus configured to allow knife member (1340) to translate distally to a point where cutting edge (1342) is distal to deck surface (1352).

In the present example, a plurality of stand-off features (1360) protrude upwardly from deck surface (1352). Stand-off features (1360) each comprise a wall (1364) that partially wraps around an end of an inner staple opening (1324) and an end of an outer staple opening (1324), with a zig-zag configuration that is identical to the configuration of stand-off features (560) described above.

Deck member (1350) of the present example also includes an upwardly protruding annular wall (1354). Annular wall (1354) of this example is configured and operable identically to annular wall (592) described above. An annular recess (1390) is formed between annular wall (1354) and stand-off features (1360). In some other versions, annular wall (1354) is connected directly to stand-off features (1360). It should also be understood that deck member (1350) may be divided into zones like the zones described above. For instance, deck member (1350) may have stand-off features (1360) located in one angular region of deck member (1350) (e.g., similar to zones (550, 750) described above); with another angular region of deck member (1350) either being flat (e.g., similar to zone (510) described above) or having less-pronounced versions of stand-off features (1360) (e.g., similar to zone (710) described above. Alternatively, stand-off features (1360) may extend around the full angular range of deck member (1350).

It should also be understood that stand-off features (1360) may provide tissue engagement effects similar to those provided by other tissue engagement features described herein, including but not limited to stand-off features (560). Thus, stand-off features (1360) may reduce the total pressure that would otherwise be applied to tissue compressed against deck member (1350), enhance the gripping of tissue that is compressed against deck member (1350), and/or provide other tissue engagement effects.

In contrast to stand-off features (560) described above, stand-off features (1360) of the present example are partially deformable. In particular, an outer region of stand-off features (1360) is formed primarily by an elastomeric member (1370) while an inner region of stand-off features (1360) is formed primarily by a rigid base member (1380). As best seen in FIG. 25, deck member (1350) provides a sloped interface between rigid base member (1380) and elastomeric member (1370), such that the inner region of elastomeric member (1370) is thinner than the outer region of elastomeric member (1370), with wall (1364) still providing a flat distal surface trough which staples (90) exit.

FIG. 26 shows anvil (400) compressing layers of tissue ($L_5$, $L_6$) against deck member (1350). As shown, elastomeric member (1370) compressibly deforms against layer of tissue ($L_6$). It should be understood that even with elastomeric member (1370) being compressible, stand-off features (1360) may still provide an enhanced grip of tissue ($L_6$) at least during an initial stage of compression of tissue ($L_5$, $L_6$). The rigidity of base member (1380), combined with the reduced thickness of elastomeric member (1370) at the inner region of stand-off features (1360), and the presence of recess (1390), may further provide an enhanced grip of tissue ($L_6$) during the full range of compression of tissue ($L_5$, $L_6$). The deformation of elastomeric member (1370) may further allow deck member (1350) to provide a pressure profile against layers of tissue ($L_5$, $L_6$) that varies along the radial extent of deck member (1350). In particular, deck member (1350) may provide greater compression of tissue ($L_5$, $L_6$) at the inner region of deck member (1350) as compared to the outer region of deck member (1350). This varying compression may further squeeze tissue ($L_5$, $L_6$) radially outwardly as tissue ($L_5$, $L_6$) is being compressed between deck member (1350) and anvil (400).

In addition to providing a different tissue gripping profile and a varying pressure profile against tissue, elastomeric member (1370) may also reduce the risk of stand-off features (1360) snagging on tissue (T) as stapling head assembly (1300) is inserted into a patient's colon (C). In particular, in the event that the outer regions of stand-off features (1360) encounter a fold (F) of tissue (T) or a region of tissue (T) that is adjacent to the patient's sacrum (S), elastomeric member (1370) may simply deform to absorb the forces impinged against stand-off features (1360). Thus, the inclusion of elastomeric member (1370) may provide a reduced risk of tissue damage as compared to the risk posed by versions of stand-off features (1360) that are entirely rigid.

Figure 27:
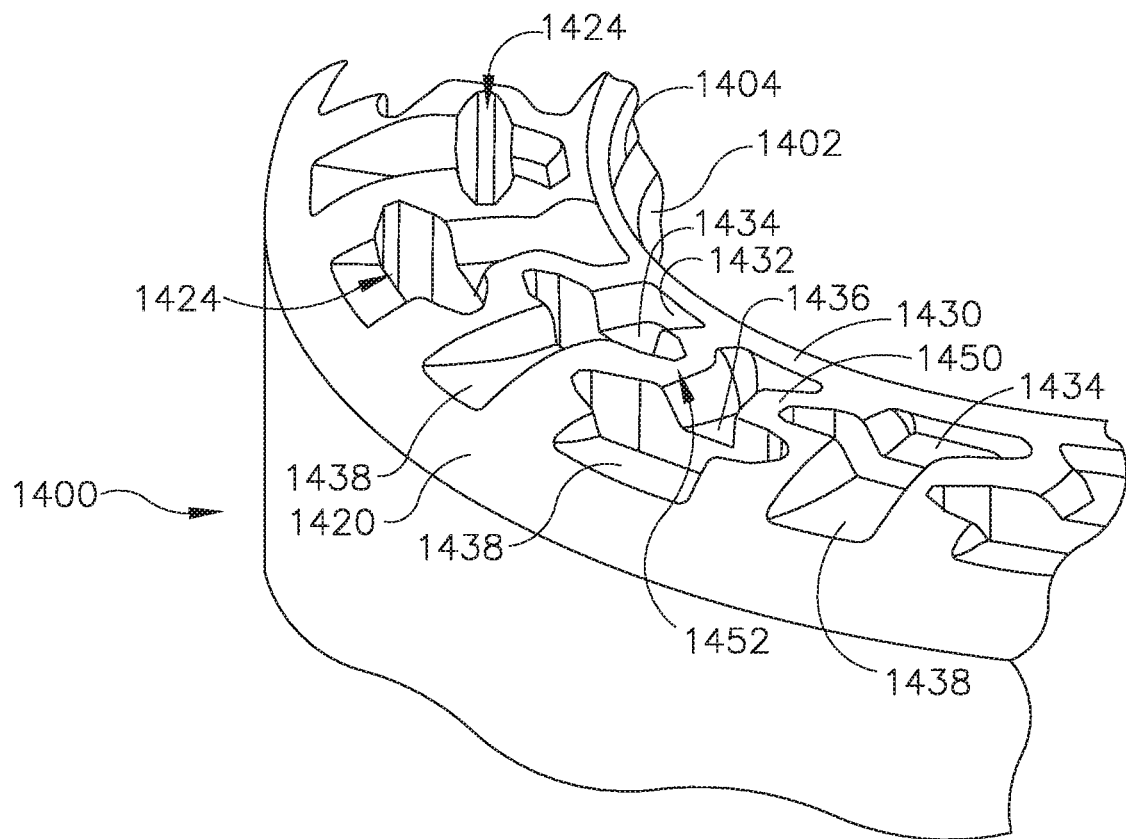
FIG. 27 depicts a partial perspective view of another exemplary alternative stapling head assembly that may be incorporated into the circular stapler of FIG. 1.
Figure 28:
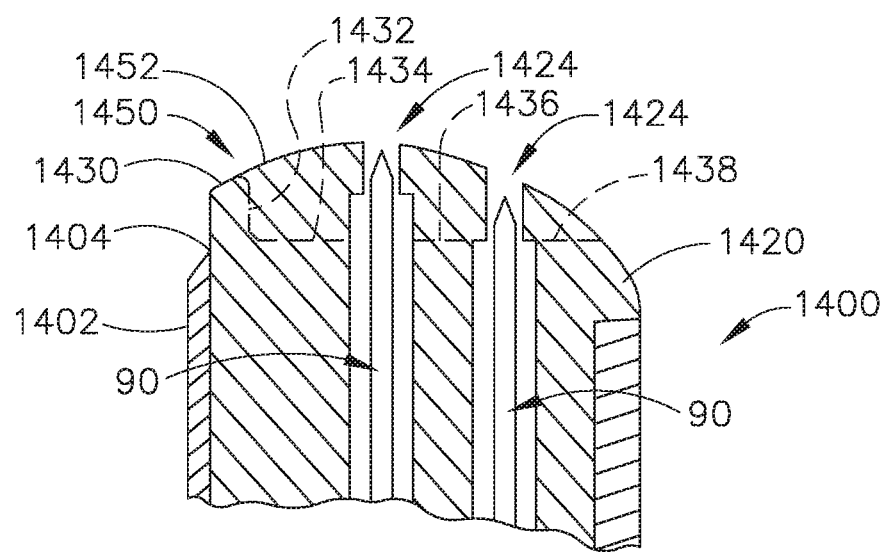
FIG. 28 depicts a partial cross-sectional view of the stapling head assembly of FIG. 27.

H. Exemplary Staple Deck Member with Combination of Rigid and Elastomeric Features FIGS. 27-28 show another exemplary stapling head assembly (1400) that may be readily incorporated into instrument (10) in place of stapling head assembly (300). Stapling head assembly (1400) is substantially identical to stapling head assembly (300) described above, except for the differences described below. Stapling head assembly (1400) of the present example comprises a curved deck surface (1450) presenting a rounded outer edge (1420). A plurality of staple openings (1424) are formed through deck surface (1450).

While deck surface (1450) has a generally curved profile in this example, deck surface (1450) defines a set of flat surfaces (1434, 1436, 1438) adjacent to staple openings (1424). In particular, flat surfaces (1434) are located inboard of each inner staple opening (1424). Flat surfaces (1436) are located inboard of each outer staple opening (1424). Each flat surface (1436, 1434) is adjacent to a corresponding inner wall (132) that leads to an inner annular portion (1430). Inner annular portion (1430) is configured to function similar to annular wall (592), such that inner annular portion (1430) is configured to compress a partially annular region of tissue against anvil (400), thereby providing assistance for edge (1404) of knife member (1402) to shear tissue. Flat surfaces (1438) are located outboard of each inner and outer staple opening (1424). Flat surfaces (1438) transition directly to rounded outer edge (1420).

Deck surface (1450) also defines a zig-zag wall (1452) that partially wraps around ends of staple openings (1424). It should be understood that the recessed aspect of flat surfaces (1434, 1436, 1438) relative to walls (1452) will provide regions for tissue to enter as the tissue is compressed against deck surface (1450) by anvil (400). Thus, zig-zag walls (1452) may provide tissue engagement effects similar to those described above, including reducing the total pressure that would otherwise be applied to tissue compressed against deck member (1450), enhancing the gripping of tissue that is compressed against deck member (1450), and/or providing other tissue engagement effects.

It should also be understood that the curved profile of deck surface (1450) may provide effects similar to those described above with respect to deck surface (1220). In particular, the curvature of deck surface (1450) may provide variable pressure to the tissue compressed between deck surface (1450) and anvil (400). Moreover, due to the curvature of deck surface (1450), deck surface (1450) may tend to squeeze the tissue radially outwardly as the tissue is compressed between deck surface (1450) and anvil (400).

I. Exemplary Staple Deck Member with Tissue Engagement Features and Staple Driver Guard Features In some conventional circular staplers, there may be a tendency for features of an actuated staple driver to protrude distally from the deck surface of the stapling head assembly after the stapling head assembly has been actuated. In some instances, these protruding staple driver features may be sharp or have some other structural configuration that may tend to damage tissue. This risk of tissue damage from exposed features of staple driver features may be present immediately after the stapling head assembly is actuated (i.e., the exposed staple driver features may damage the tissue that is still compressed between the anvil and the staple deck). In addition, there may be a risk that such staple driver features will snag on tissue as the actuated stapling head assembly is removed from the patient's colon (C) or other anatomical structure. It may therefore be desirable to modify the deck of the stapling head assembly to prevent any features of an actuated staple driver to protrude distally from the deck surface after the stapling head assembly has been actuated.

Figure 29:
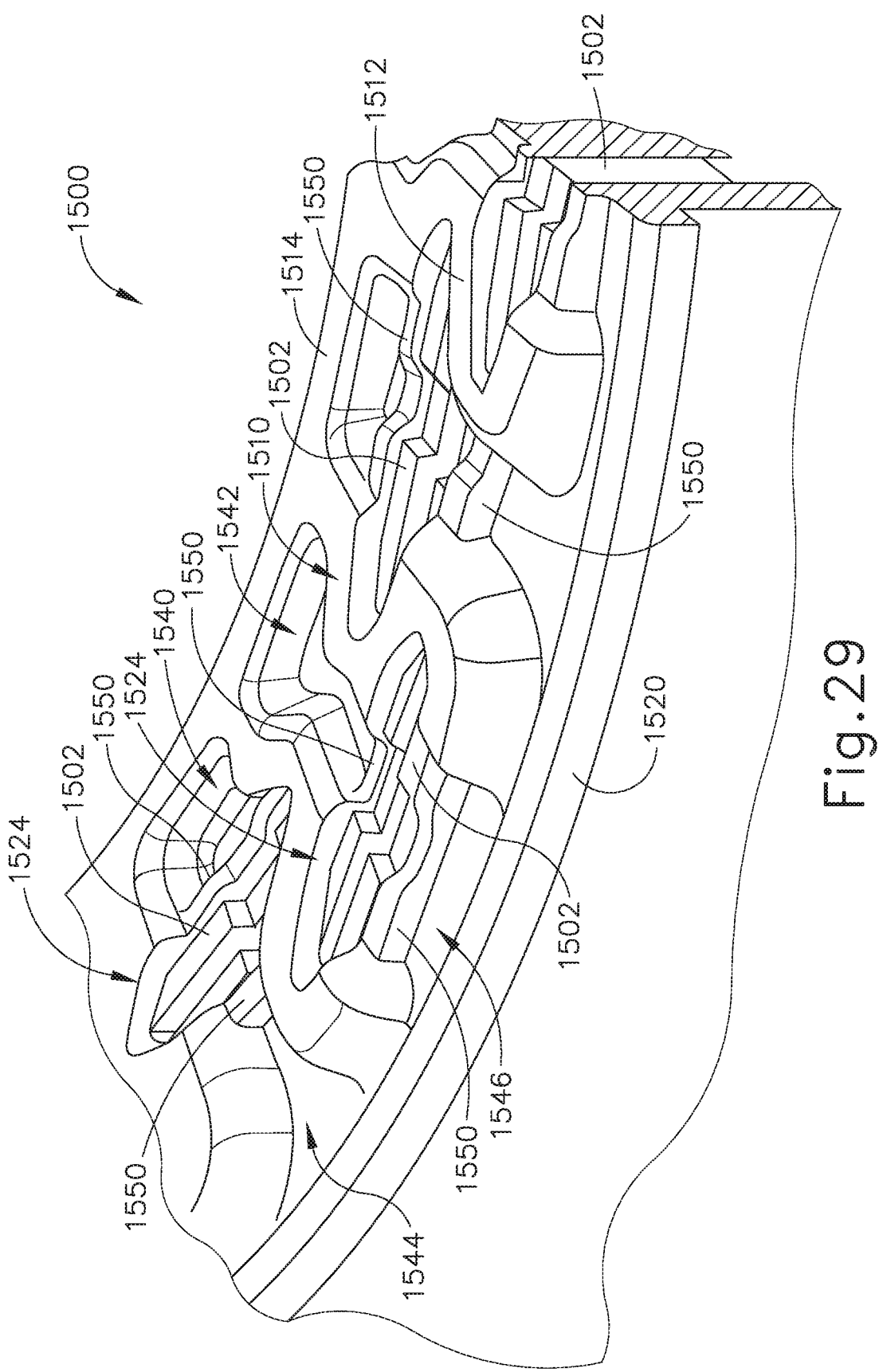
FIG. 29 depicts a partial perspective view of another exemplary alternative stapling head assembly that may be incorporated into the circular stapler of FIG. 1.

FIG. 29 shows another exemplary alternative deck member (1500) that may be readily incorporated into stapling head assembly (300) in place of deck member (320). Deck member (1500) of this example comprises a deck surface (1510) defining a plurality of staple openings (1524). Deck surface (1510) includes a zig-zag walls (1512) and an inner annular portion (1514). Zig-zag walls (1512) partially wrap around ends of staple openings (1424). Inner annular portion (1514) is configured to function similar to annular wall (592), such that inner annular portion (1514) is configured to compress a partially annular region of tissue against anvil (400), thereby providing assistance for a cutting edge of a knife member to shear tissue. Deck surface (1510) further defines an inner recess (1540) inboard of each inner staple opening (1524) and an outer recess (1544) that is outboard of each inner staple opening (1524). Similarly, deck surface (1510) further defines an inner recess (1542) inboard of each outer staple opening (1524) and an outer recess (1546) that is outboard of each outer staple opening (1524). Outer recesses (1544, 1546) are contiguous with a rounded outer edge (1520) of deck member (1500).

Deck member (1550) also includes a set of inner walls (1550) separating each inner staple opening (1524) from corresponding recesses (1540, 1544). Inner walls (1550) are recessed relative to deck surface (1510) but are proud relative to recesses (1540, 1544). Similarly, a set of wall (1550) separates each outer staple opening (1524), from corresponding recesses (1542, 1546). Again, inner walls (1550) are recessed relative to deck surface (1510) but are proud relative to recesses (1542, 1546).

It should be understood that the combination of zig-zag walls (1512) and recesses (1540, 1542, 1544, 1546) may provide tissue engagement effects similar to those described above, including reducing the total pressure that would otherwise be applied to tissue compressed against deck member (1500), enhancing the gripping of tissue that is compressed against deck member (1500), and/or providing other tissue engagement effects.

It should also be understood that zig-zag walls (1512) and walls (1550) may cooperate to shield deployed staple drivers (1502). In particular, as shown in FIG. 29, all of the structural features of the deployed staple drivers (1502) are recessed relative to zig-zag walls (1512) and walls (1550) in this example. Zig-zag walls (1512) and walls (1550) will thus prevent staple drivers (1502) from snagging or otherwise damaging tissue after staple drivers (1502) have reached the fully deployed position shown in FIG. 29.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly has a distal end; (c) a stapling head assembly located at the distal end of the shaft assembly, wherein the stapling head assembly comprises: (i) an annular deck member defining an inner diameter and an outer diameter, wherein the deck member comprises: (A) a first deck surface, wherein the first deck surface has a curved profile defined by a curve extending from the inner diameter of the deck member to the outer diameter of the deck member, (B) an outer annular array of staple openings, and (C) an inner annular array of staple openings, (ii) a plurality of staples, and (iii) a driver operable to drive the staples through the staple openings; and (d) an anvil, wherein the anvil is operable to compress tissue against the first deck surface.

Example 2

The apparatus of Example 1, wherein the curve presents a distal-most region located between the inner diameter and the outer diameter.

Example 3

The apparatus of Example 2, wherein the distal-most region of the curve is located closer to the inner diameter than to the outer diameter.

Example 4

The apparatus of any one or more of Examples 1 through 3, wherein the deck member further comprises a second deck surface, wherein the second deck surface is recessed relative to the first deck surface.

Example 5

The apparatus of Example 4, wherein the deck member further comprises a plurality of stand-off features protruding from the second deck surface, wherein the first deck surface is located on the stand-off features.

Example 6

The apparatus of Example 5, wherein the stand-off features comprise walls having a zig-zag shape.

Example 7

The apparatus of any one or more of Examples 5 through 6, wherein an inner portion of each stand-off feature partially surrounds an end of a corresponding staple opening of the inner annular array of staple openings, wherein an outer portion of each stand-off feature partially surrounds an end of a corresponding staple opening of the outer annular array of staple openings.

Example 8

The apparatus of any one or more of Examples 5 through 7, further comprising an inner annular wall extending upwardly from the second surface, wherein the inner annular wall is located at the inner diameter of the deck member.

Example 9

The apparatus of Example 8, wherein a portion of the first surface and a distal edge of the inner annular wall are coplanar.

Example 10

The apparatus of any one or more of Examples 8 through 9, wherein the deck member defines an annular recess between the stand-off features and the inner annular wall.

Example 11

The apparatus of any one or more of Examples 8 through 10, wherein the inner annular wall has a distal edge, wherein the distal edge of the annular wall is located along the curve of the first deck surface.

Example 12

The apparatus of any one or more of Examples 4 through 11, wherein the stapling head assembly defines a longitudinal axis, wherein second deck surface is obliquely oriented relative to the longitudinal axis.

Example 13

The apparatus of Example 12, wherein the second deck surface is obliquely oriented such that an outermost portion of the second deck surface is positioned distally relative to an innermost portion of the deck surface, such that the second deck surface slopes proximally from the outermost portion toward the innermost portion.

Example 14

The apparatus of any one or more of Examples 1 through 13, wherein the deck member further comprises a second deck surface extending along a first angular range, wherein the second deck surface is flat, wherein the first deck surface extends along a second angular range.

Example 15

The apparatus of Example 14, wherein the shaft assembly has a curved region with an inner curve and an outer curve, wherein the first angular range is angularly positioned to correspond with the outer curve, wherein the second angular range is angularly positioned to correspond with the inner curve.

Example 16

An apparatus, comprising: (a) a body; (b) a shaft assembly extending distally from the body, wherein the shaft assembly has a distal end; (c) a stapling head assembly located at the distal end of the shaft assembly, wherein the stapling head assembly defines a longitudinal axis, wherein the stapling head assembly comprises: (i) an annular deck member defining an inner diameter and an outer diameter, wherein the deck member comprises: (A) a deck surface, wherein a portion of the deck surface is obliquely oriented relative to the longitudinal axis such that the deck surface is sloped along a radially extending path, (B) an outer annular array of staple openings, and (C) an inner annular array of staple openings, (ii) a plurality of staples, and (iii) a driver operable to drive the staples through the staple openings; and (d) an anvil, wherein the anvil is operable to compress tissue against the first deck surface.

Example 17

The apparatus of Example 16, wherein the deck surface is sloped such that the deck surface slopes proximally from an outer region of the deck surface toward an inner region of the deck surface.

Example 18

The apparatus of any one or more of Examples 16 through 17, wherein the deck member further comprises a distal surface positioned distally in relation to the deck surface.

Example 19

The apparatus of Example 18, wherein the distal surface has a curved profile defined by a curve extending from the inner diameter of the deck member to the outer diameter of the deck member.

Example 20

A surgical stapling head assembly, comprising: (a) an annular deck member defining an inner diameter and an outer diameter, wherein the deck member comprises: (i) a first deck surface, wherein the first deck surface has a curved profile defined by a curve extending from the inner diameter of the deck member to the outer diameter of the deck member, (ii) a second deck surface, wherein a portion of the deck surface is obliquely oriented relative to the longitudinal axis such that the deck surface is sloped along a radially extending path, (iii) an outer annular array of staple openings, and (iv) an inner annular array of staple openings; (b) a plurality of staples; and (c) a driver operable to drive the staples through the staple openings.

IV. Miscellaneous

It should be understood that the teachings above may be readily combined with the teachings of U.S. patent application Ser. No. 15/350,513, entitled "Circular Surgical Stapler with Recessed Deck and Raised Circumferential Edges," filed on Nov. 14, 2016 and published as U.S. Pat. Pub. No. 2018/0132853 on May 17, 2018, the disclosure of which is incorporated by reference herein. Various suitable ways in which the teachings herein and the teachings of U.S. patent application Ser. No. 15/350,513 may be combined will be apparent to those of ordinary skill in the art.

It should also be understood that the teachings above may be readily combined with the teachings of U.S. patent application Ser. No. 15/350,621, entitled "Staple Pocket Configurations for Circular Surgical Stapler," filed on Nov. 14, 2016 and published as U.S. Pat. Pub. No. 2018/0132849 on May 17, 2018, the disclosure of which is incorporated by reference herein. Various suitable ways in which the teachings herein and the teachings of U.S. patent application Ser. No. 15/350,621 may be combined will be apparent to those of ordinary skill in the art.

It should also be understood that the teachings above may be readily combined with the teachings of U.S. patent application Ser. No. 15/350,624, entitled "Circular Surgical Stapler with Angularly Asymmetric Deck Features," filed on Nov. 14, 2016 and published as U.S. Pat. Pub. No. 2018/0132854 on May 17, 2018, the disclosure of which is incorporated by reference herein. Various suitable ways in which the teachings herein and the teachings of U.S. patent application Ser. No. 15/350,624 may be combined will be apparent to those of ordinary skill in the art.

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned the disclosure of which is incorporated by reference herein; U.S. Pub. No. 2014/0144969, entitled "Pivoting Anvil for Surgical Circular Stapler," published May 29, 2014, now issued as U.S. Pat. No. 9,498,22 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A stapling head assembly configured for use with a surgical stapler, comprising:
    (a) an annular deck member operable to compress tissue against an anvil, wherein the deck member defines a central axis and comprises:
        (i) an annular first deck surface,
        (ii) an annular second deck surface disposed radially inwardly of the first deck surface, wherein the second deck surface is raised distally relative to the first deck surface, (iii) an annular array of staple openings formed in the second deck surface,
(iv) an arrangement of inner recesses formed in the second deck surface, wherein at least a portion of the arrangement of inner recesses is disposed radially inwardly of the array of staple openings, and
(v) an arrangement of outer recesses formed in the second deck surface radially outwardly of the arrangement of inner recesses, wherein the inner recesses are isolated from the outer recesses;
(b) a plurality of staples disposed within the staple openings; and
(c) a staple driver, wherein the staple driver is operable to drive the staples distally through the staple openings and into tissue compressed between the deck member and the anvil,
wherein the deck member is configured to compress tissue against the anvil such that the deck member exerts a lesser degree of compression on tissue portions that overlie one of the inner recesses or one of the outer recesses than tissue portions that overlie the staple openings.

2. The stapling head assembly of claim 1, wherein the deck member comprises a radially inner annular array of staple openings and a radially outer annular array of staple openings formed in the second deck surface.

3. The stapling head assembly of claim 2, wherein a radially outermost portion of each inner recess extends between a respective pair of staple openings of the inner array of staple openings.

4. The stapling head assembly of claim 2, wherein a radially innermost portion of each outer recess extends between a respective pair of staple openings of the outer array of staple openings.

5. The stapling head assembly of claim 1, wherein each of the outer recesses has a first shape, wherein each of the inner recesses has a second shape different than the first shape.

6. The stapling head assembly of claim 1, wherein the arrangement of inner recesses comprises a plurality of triangular recesses.

7. The stapling head assembly of claim 1, wherein the outer recesses open to the first deck surface.

8. The stapling head assembly of claim 1, wherein each of the inner recesses is bounded by a floor, wherein the floors are coplanar with the first deck surface.

9. The stapling head assembly of claim 8, wherein each of the inner recesses is bounded by a sidewall that is obliquely angled relative to the respective floor.

10. The stapling head assembly of claim 1, wherein each of the inner recesses is circumferentially offset from each adjacent outer recess.

11. The stapling head assembly of claim 1, wherein the deck member comprises a first zone extending along a first angular range of the deck member, and a second zone extending along a second angular range of the deck member, wherein the arrangement of outer recesses is disposed within the first zone and the second zone.

12. The stapling head assembly of claim 11, wherein the arrangement of inner recesses is disposed within the second zone and not the first zone.

13. The stapling head assembly of claim 1, wherein the deck member further comprises a plurality of angled transition surfaces extending between the first deck surface and the second deck surface.

14. The stapling head assembly of claim 1, wherein the inner recesses are isolated from the staple openings.

15. A surgical stapler comprising:
(a) a body;
(b) a shaft assembly extending distally from the body; and
(c) the stapling head assembly of claim 1, wherein the stapling head assembly is located at a distal end of the shaft assembly.

16. A stapling head assembly configured for use with a surgical stapler, comprising:
(a) an annular deck member operable to compress tissue against an anvil, wherein the deck member defines a central axis and comprises:
(i) an annular first deck surface,
(ii) an annular second deck surface disposed radially inwardly of the first deck surface, wherein the second deck surface is raised distally relative to the first deck surface,
(iii) an annular array of staple openings formed in at least one of the first deck surface or the second deck surface,
(iv) an arrangement of outer recesses formed in the second deck surface,
(v) an arrangement of inner recesses formed in the second deck surface radially inwardly of the arrangement of outer recesses,
(vi) a first zone that extends circumferentially about the central axis along a first angular range of the deck member, and
(vii) a second zone that extends circumferentially about the central axis along a second angular range of the deck member,
wherein the arrangement of outer recesses is disposed within the first zone and the second zone,
wherein the arrangement of inner recesses is disposed within the second zone and not the first zone,
(b) a plurality of staples disposed within the staple openings; and
(c) a staple driver, wherein the staple driver is operable to drive the staples distally through the staple openings and into tissue compressed between the deck member and the anvil.

17. The stapling head assembly of claim 16, wherein the deck member comprises an inner array of staple openings and an outer array of staple openings, wherein a radially outermost portion of each inner recess extends between a respective pair of staple openings of the inner array of staple openings, wherein a radially innermost portion of each outer recess extends between a respective pair of staple openings of the outer array of staple openings.

18. The stapling head assembly of claim 16, wherein arrangement of inner recesses comprises a plurality of triangular recesses.

19. A stapling head assembly configured for use with a surgical stapler, comprising:
(a) an annular deck member operable to compress tissue against an anvil, wherein the deck member defines a central axis and comprises:
(i) an annular first deck surface,
(ii) an annular second deck surface disposed radially inwardly of the first deck surface, wherein the second deck surface is raised distally relative to the first deck surface,
(iii) an annular array of staple openings formed in the second deck surface, and
(iv) a plurality of recesses formed in the second deck surface and shaped triangularly in a transverse plane with respect to the central axis, wherein a radially outermost portion of each recess extends between a respective pair of the staple openings, (b) a plurality of staples disposed within the staple openings; and (c) a staple driver, wherein the staple driver is operable to drive the staples distally through the staple openings and into tissue compressed between the deck member and the anvil, wherein the deck member is configured to compress tissue against the anvil such that the deck member exerts a lesser degree of compression on tissue portions that overlie the triangular recesses than tissue portions that overlie the staple openings.

20. The stapling head assembly of claim 19, wherein the deck member further comprises a plurality of outer recesses formed in the second deck surface, wherein the plurality of outer recesses is disposed radially outwardly of the plurality of triangular recesses.

\* \* \* \* \*